United States Patent
Inoue

(10) Patent No.: US 10,918,451 B2
(45) Date of Patent: Feb. 16, 2021

(54) MEDICAL INSTRUMENT HOLDING DEVICE, MEDICAL SYSTEM, OPERATING METHOD OF MEDICAL INSTRUMENT HOLDING DEVICE, AND OPERATING METHOD OF MEDICAL SYSTEM

(71) Applicant: Olympus Corporation, Hachioji (JP)

(72) Inventor: Shintaro Inoue, Cambridge, MA (US)

(73) Assignee: OLYMPUS CORPORATION, Tokyo (JP)

( * ) Notice: Subject to any disclaimer, the term of this patent is extended or adjusted under 35 U.S.C. 154(b) by 251 days.

(21) Appl. No.: 16/218,699

(22) Filed: Dec. 13, 2018

(65) Prior Publication Data

US 2019/0110849 A1    Apr. 18, 2019

Related U.S. Application Data

(63) Continuation of application No. PCT/JP2016/069996, filed on Jul. 6, 2016.

(51) Int. Cl.
| | | |
|---|---|---|
| A61B 17/00 | (2006.01) | |
| A61B 34/00 | (2016.01) | |
| A61B 34/30 | (2016.01) | |
| A61B 1/005 | (2006.01) | |

(52) U.S. Cl.
CPC ............ *A61B 34/74* (2016.02); *A61B 34/30* (2016.02); *A61B 1/0055* (2013.01); *A61B 34/25* (2016.02); *A61B 2034/302* (2016.02)

(58) Field of Classification Search
CPC ....... A61B 34/74; A61B 34/30; A61B 1/0055; A61B 2034/302; A61B 17/00;

(Continued)

(56) References Cited

U.S. PATENT DOCUMENTS 6,212,443 B1    4/2001  Nagata et al.
2008/0287926 A1*  11/2008  Abou El Kheir .. A61B 17/3421
                                                                        606/1

(Continued)

FOREIGN PATENT DOCUMENTS

JP        60-252911        12/1985
JP        09-085656         3/1997

(Continued)

OTHER PUBLICATIONS

International Search Report and Written Opinion from International Application No. PCT/JP2016/069996, dated Sep. 20, 2016.

*Primary Examiner* — Dalena Tran

(74) *Attorney, Agent, or Firm* — Scully, Scott, Murphy & Presser, P.C.

(57) ABSTRACT

The disclosed technology is directed to a medical instrument holding device comprises a holding portion configured to hold a first medical instrument having a first insertion portion to be inserted into an abdominal cavity of a patient. An arm is connected to the holding portion and including at least one joint. A base is connected to a proximal end side of the arm. A first sensor is configured to detect an external force caused by a second insertion portion of a second medical instrument in the abdominal cavity. A controller is configured to generate a first control signal for actuating the arm based on the external force detected by the first sensor.

12 Claims, 14 Drawing Sheets

(58) Field of Classification Search
CPC ..... A61B 17/00234; B25J 13/088; B25J 5/00; B25J 18/00; B25J 3/04; Y10S 901/09; Y10S 901/34; Y10S 901/41; Y10S 901/01; Y10S 901/15; Y10S 901/19; Y10S 901/30; Y10S 901/02
USPC ........... 700/245; 128/899; 901/9, 15, 28, 46; 606/1, 130; 318/568.11, 568.21, 568.22, 318/560; 600/427, 104, 117, 118, 12, 600/184, 114, 145, 201
See application file for complete search history.

(56) References Cited

U.S. PATENT DOCUMENTS

| | | | |
|---|---|---|---|
| 2010/0160724 A1* | 6/2010 | Prisco | A61B 34/35 600/101 |
| 2011/0230869 A1 | 9/2011 | Altamirano | |
| 2013/0041360 A1* | 2/2013 | Farritor | A61B 18/1445 606/29 |

FOREIGN PATENT DOCUMENTS

| | | |
|---|---|---|
| JP | 2002-017752 | 1/2002 |
| JP | 2003-126116 | 5/2003 |
| JP | 2005-192743 | 7/2005 |
| JP | 2009-023047 | 2/2009 |
| JP | 2012-515025 | 7/2012 |
| JP | 2015-002922 | 1/2015 |
| WO | 2010081482 | 7/2010 |
| WO | 2014199415 | 12/2014 |
| WO | 2015079775 | 6/2015 |

* cited by examiner

MEDICAL INSTRUMENT HOLDING DEVICE, MEDICAL SYSTEM, OPERATING METHOD OF MEDICAL INSTRUMENT HOLDING DEVICE, AND OPERATING METHOD OF MEDICAL SYSTEM

CROSS-REFERENCE TO RELATED APPLICATION

This application is a continuation application of PCT Application No. PCT/JP2016/069996 filed on Jul. 6, 2016, which is hereby incorporated by reference in its entirety.

TECHNICAL FIELD

The present disclosure relates to a medical instrument holding device, a medical system, an operating method of the medical instrument holding device, and an operating method of the medical system.

DESCRIPTION OF THE RELATED ART

Medical manipulator devices that perform a surgical operation by actuating a plurality of arms are conventionally known. To a distal end portion of each arm of such a medical manipulator device, a medical instrument or an auxiliary instrument (hereinafter simply called "auxiliary instrument") is attached to assist an operator's surgical procedures. In general, this auxiliary instrument is operated by an assistant to the operator. The operator, therefore, performs a surgical procedure by the medical instrument operated by himself or herself while giving instructions to the assistant as to how to move the auxiliary instrument attached to the arm. A situation may, however, arise that the operator's instructions may not be conveyed well to the assistant and the auxiliary instrument operated by the assistant may not be moved as intended by the operator.

Hence, medical manipulator devices have been proposed that can operate an auxiliary instrument, which is attached to an arm, by a medical instrument held by an operator. For example, Japanese Patent Laid-open No. 2003-126116 discloses a medical manipulator device, which includes a first surgical instrument disposed on a distal end portion of a manipulator, positioning means setting a position of the first surgical instrument, and a second surgical instrument having a grip to be grasped by an operator. The second surgical instrument has operation means that has a switch for outputting an instruction to control movement of the positioning means, and the switch is arranged at a position where the operator can operate the switch with the hand that is grasping the grip. Accordingly, the operator can move the first surgical instrument to his or her intended position by operating the switch of the second surgical instrument while operating the second surgical instrument grasped by himself or herself.

With the medical manipulator device described in Japanese Patent Laid-open No. 2003-126116, however, the operator controls the position of the first surgical instrument by operating the switch arranged at the grip of the second surgical instrument so that the operator is required to operate the switch while taking into consideration the correspondence between the operating direction of the switch and the moving direction of the first surgical instrument. It is, however, cumbersome to move the first surgical instrument to a desired position through the switch of the second surgical instrument.

Accordingly, there is a need for a medical instrument holding device and a medical system, both of which can be easily moved by an operator, to a desired position, an auxiliary instrument held on an arm portion, an operating method of the medical instrument holding device, and an operating method of the medical system.

BRIEF SUMMARY OF EMBODIMENTS

According to a first embodiment of the present disclosure, a medical instrument holding device includes a holding portion configured to hold a first medical instrument having a first end effector, an arm portion having a plurality of joints and a distal end portion connected to the holding portion, a base portion connected to a proximal end portion of the arm portion, a force detecting portion configured to detect an external force applied to the first medical instrument held on the holding portion, and a control unit configured to generate, based on the external force detected by the force detecting portion, control signals to actuate the joints.

According to a second embodiment of the present disclosure, in the medical instrument holding device according to the first embodiment, the first medical instrument may include a first distal end portion on which the first end effector is arranged, a first proximal end portion held on the holding portion, and a first insertion portion extending from the first proximal end portion to the first distal end portion. The force detecting portion may be configured to detect the external force applied only to the first insertion portion or the first distal end portion.

According to a third embodiment of the present disclosure, in the medical instrument holding device according to the second embodiment, the first medical instrument may include at least one contacted portion at the first insertion portion or the first distal end portion. The force detecting portion may be configured to detect the external force applied to the contacted portion.

According to a fourth embodiment of the present disclosure, in the medical instrument holding device according to the third embodiment, the contacted portion may include an operation instructing portion configured to enable operation of the first end effector.

According to a fifth embodiment of the present disclosure, the medical instrument holding device according to the third or fourth embodiment may further include a contact detecting portion configured to detect a contacted state at the contacted portion. The control unit may be configured to generate, based on the contacted state and the external force, the control signals to actuate the joints.

According to a sixth embodiment of the present disclosure, in the medical instrument holding device according to the fifth embodiment, the control unit may be configured to generate control signals to maintain the joints at the same positions if the contact detection portion has detected that the contacted portion is out of contact.

According to a seventh embodiment of the present disclosure, in the medical instrument holding device according to the fifth or sixth embodiment, the control unit may be configured to generate control signals to maintain the external force, which the force detecting portion detected a predetermined period of time before the detection of the out-of-contact by the contact detecting portion, if the contact detecting portion has detected the out-of-contact at the contacted portion subsequent to the detection of the contacted state at the contacted portion.

According to an eighth embodiment of the present disclosure, a medical system includes a medical instrument holding device, which includes a first medical instrument having a first end effector, a second medical instrument having a second end effector, a holding portion configured to hold the first medical instrument, an arm portion having a plurality of joints and a distal end portion connected to the holding portion, a base portion connected to a proximal end portion of the arm portion, a force detecting portion configured to detect an external force applied to the first medical instrument held on the holding portion, and a control unit configured to generate, based on the external force detected by the force detecting portion, control signals to actuate the joints.

According to a ninth embodiment of the present disclosure, in the medical system according to the eighth embodiment, the first medical instrument may include a first distal end portion on which the first end effector is arranged, a first proximal end portion held on the holding portion, and a first insertion portion extending from the first proximal end portion to the first distal end portion. The force detecting portion may be configured to detect the external force applied only to the first insertion portion or the first distal end portion.

According to a tenth embodiment of the present disclosure, in the medical system according to the ninth embodiment, the first medical instrument may include at least one contacted portion at the first insertion portion or the first distal end portion. The force detecting portion may be configured to detect the external force applied to the contacted portion.

According to an eleventh embodiment of the present disclosure, in the medical system according to the tenth embodiment, the force detecting portion may be configured to detect the external force occurred through contact of the second medical instrument to the contacted portion.

According to a twelfth embodiment of the present disclosure, in the medical system according to the tenth or eleventh embodiment, the contacted portion may include an operation instructing portion configured to enable operation of the first end effector by bringing the second end effector into contact with the first end effector.

According to a thirteenth embodiment of the present disclosure, in the medical system according to any one of the tenth to twelfth embodiments, the medical instrument holding device may further include a contact detecting portion configured to detect a contacted state at the contacted portion. The control unit may be configured to generate, based on the contacted state and the external force, the control signals to actuate the joints.

According to a fourteenth embodiment of the present disclosure, an operating method of a medical instrument holding device, which has a holding portion holding a first medical instrument, an arm portion having a plurality of joints, and a control unit configured to generate control signals to actuate the joints, includes a step of detecting an external force applied to the first medical instrument, a step of generating the control signals based on the detected external force, and a step of actuating the joints based on the control signals.

According to a fifteenth embodiment of the present disclosure, the operating method according to the fourteenth embodiment of the medical instrument holding device may further include a step of detecting, at the first medical instrument, a contacted state from an outside. In the step of generating the control signals, the control signals may be generated based on the contacted state and the external force.

According to a sixteenth embodiment of the present disclosure, an operating method of a medical system, which has a first medical instrument, a second medical instrument, a medical instrument holding device having a holding portion configured to hold the first medical instrument, an arm portion having a plurality of joints, and a control unit configured to generate control signals to actuate the joints, includes a step of detecting, by the second medical instrument, an external force applied to the first medical instrument, a step of generating the control signals based on the detected external force, and a step of actuating the joints based on the control signals.

According to a seventeenth embodiment of the present disclosure, the operating method according to the sixteenth embodiment of the medical system may further include a step of detecting a contacted state by the second medical instrument at the first medical instrument. In the step of generating the control signals, the control signals may be generated based on the contacted state and the external force.

According to the medical instrument holding device, the medical system, the operating method of the medical instrument holding device, and the operating method of the medical system described hereinbefore, operators can easily move, to a desired position, the medical instrument held on the arm portion.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Figure 1:
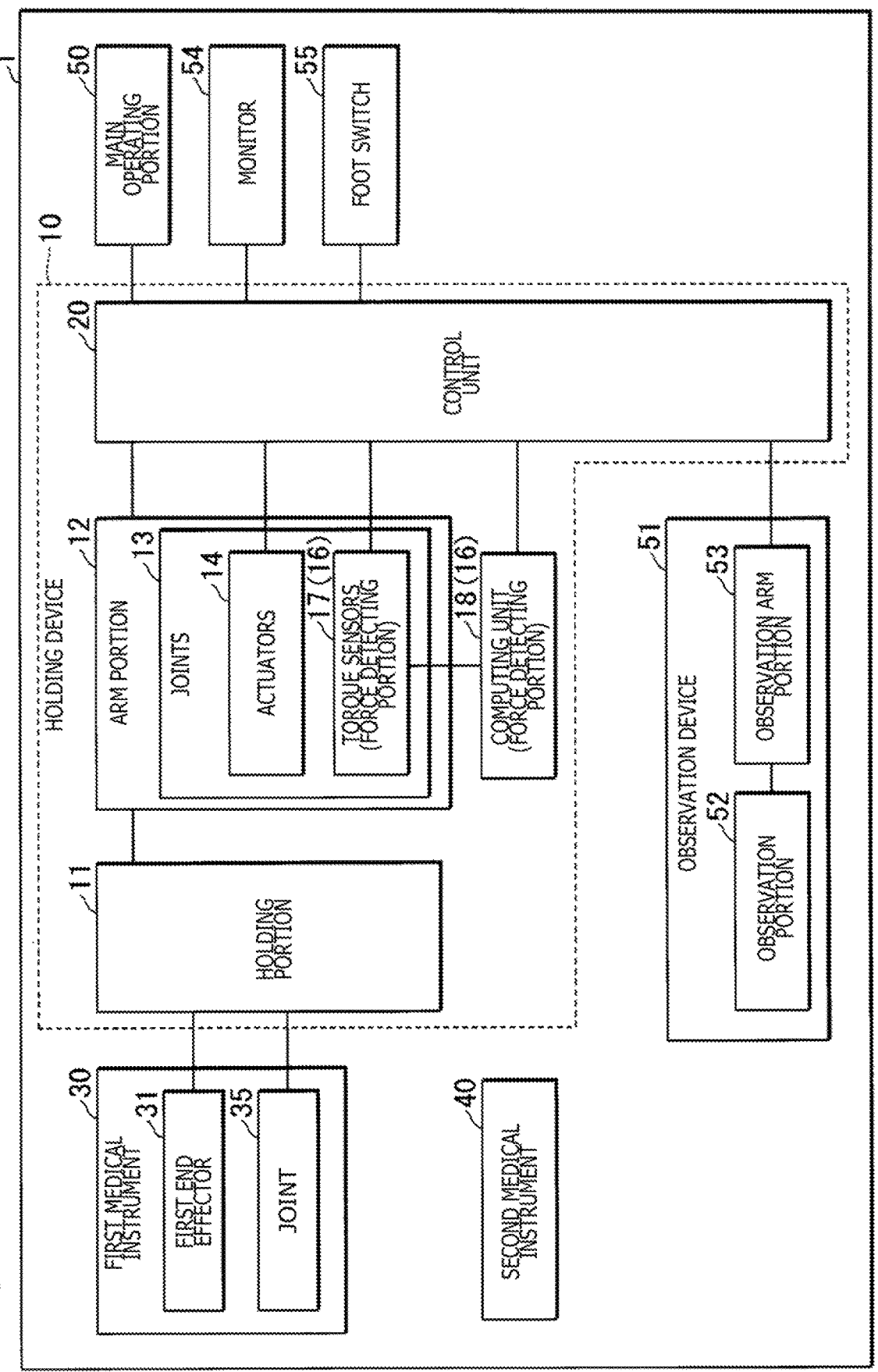
FIG. 1 is a functional block diagram of a medical system according to a first embodiment of the present disclosure.
Figure 2:
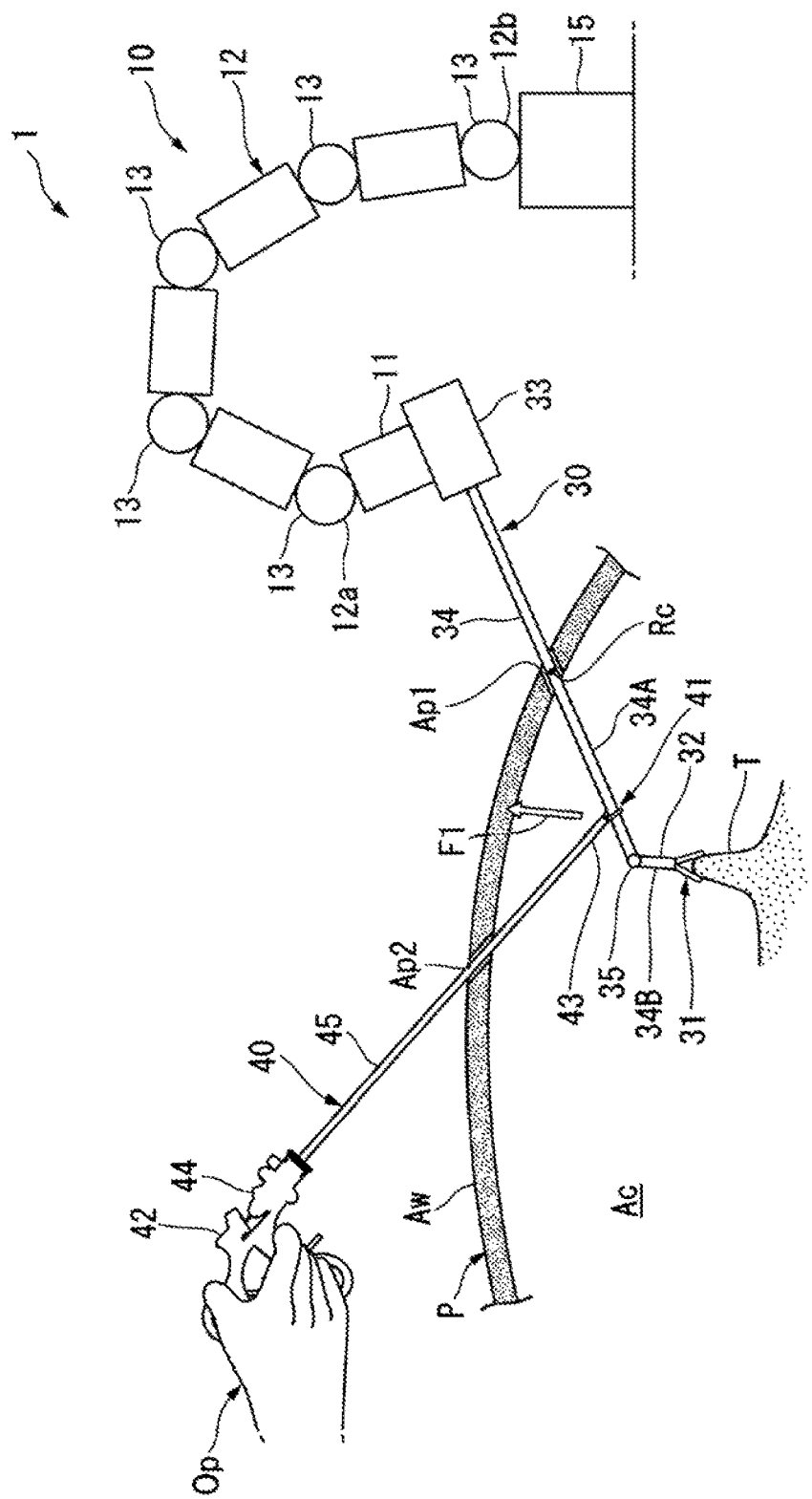
FIG. 2 is a view schematically depicting the medical system according to the first embodiment.
Figure 3:
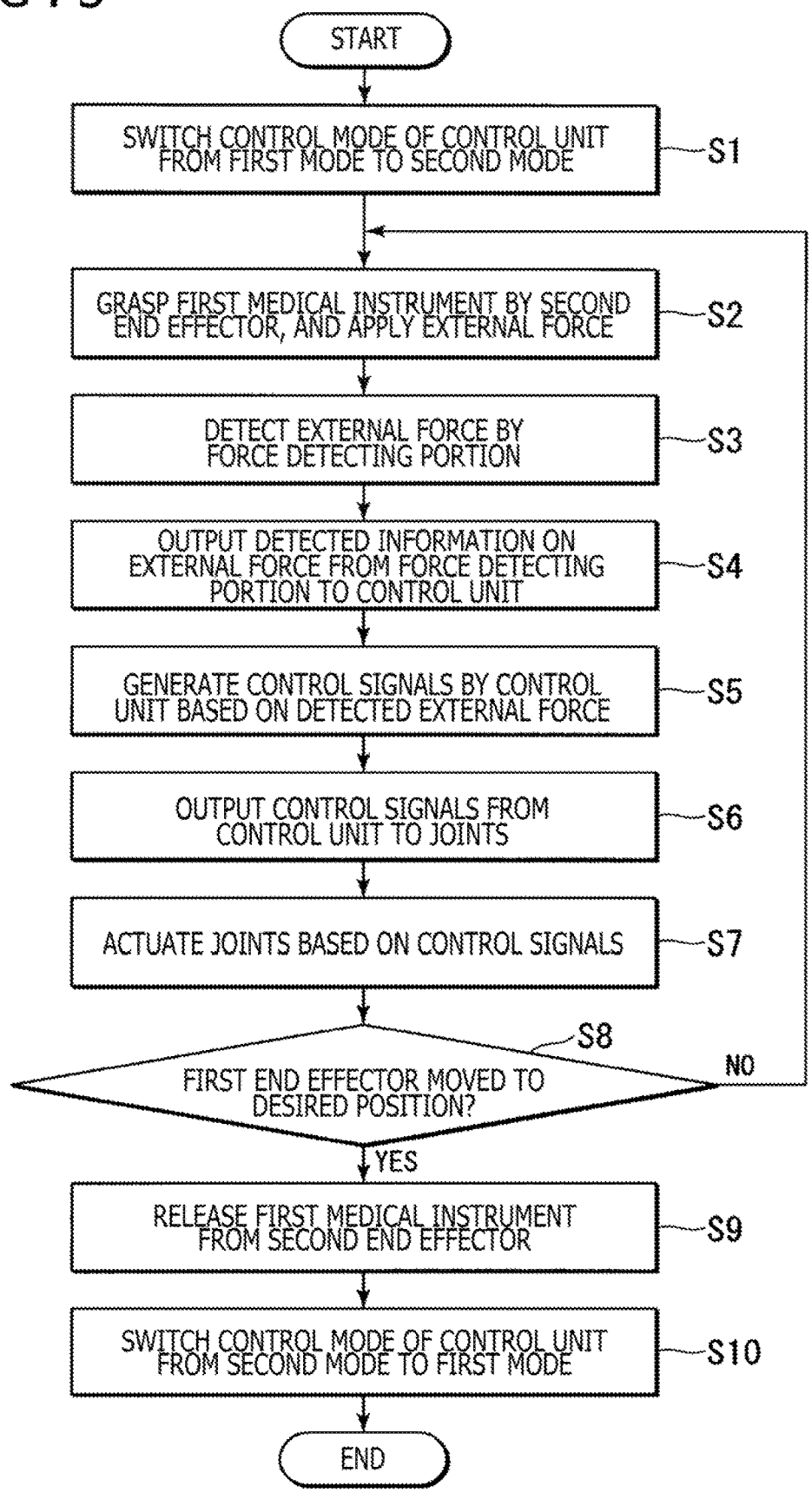
FIG. 3 is a flow chart illustrating operation of the medical system according to the first embodiment.

With reference to FIGS. 1 to 3, a description will hereinafter be made about a first embodiment of the present disclosure.

FIG. 1 is a functional block diagram of a medical system 1 according to the first embodiment. FIG. 2 is a view schematically depicting the medical system 1.

As depicted in FIGS. 1 and 2, the medical system 1 includes a medical instrument holding device (hereinafter simply called "the holding device") 10, a first medical instrument 30, and a second medical instrument 40.

The holding device 10 includes a holding portion 11, an arm portion 12, a base portion 15, a force detecting unit 16, and a control unit 20.

The holding portion 11 holds the first medical instrument 30. The holding portion 11 is configured to be connectable with the first medical instrument 30 by a connection mechanism. With the first medical instrument 30 connected to and held by the holding portion 11, a movable part of the first medical instrument 30 can be moved under control by the control unit 20.

The arm portion 12 has a plurality of joints 13, and also has a distal end portion 12a connected to the holding portion 11. The configuration and number of the joints 13 are set according to the degrees of freedom needed to perform desired treatments by the first medical instrument 30 held on the holding portion 11. A joint configuration is applied to each joint 13. Further, the arm portion 12 has a plurality of actuators 14. The actuators 14 have a configuration suited to drive the joints 13, and are arranged in the joints 13, respectively. The joints 13 can be moved by the actuators 14, respectively.

The base portion 15 is connected to a proximal end portion 12b of the arm portion 12. The base portion 15 supports the arm portion 12 so that the holding device 10 does not fall down by movement of the arm portion 12 or otherwise fail to be adequately supported.

The force detecting portion 16 detects an external force applied to the first medical instrument 30 held on the holding portion 11. In this embodiment, the force detecting portion 16 is defined by torque sensors 17 arranged in the arm portion 12 and a computing unit 18 electrically connected to the individual torque sensors 17. The torque sensors 17 detect the magnitudes of torques applied to the individual joints 13, and are arranged in the joints 13 of the arm portion 12, respectively. The computing unit 18 has a configuration capable of performing predetermined numerical calculations and the like. If an external force is applied to the first medical instrument 30, the torque sensors 17 and computing unit 18 can detect the external force by a kinematic method while using information such as the shapes or the like of the first medical instrument 30 and arm portion 12.

In addition, the force detecting portion 16 outputs the detected external force as detection information of the external force to the control unit 20. The detection information of the external force, which the force detecting portion 16 outputs, includes at least the magnitude and direction of the external force.

Based on the external force detected by the force detecting portion 16, the control unit 20 generates control signals to actuate the joints 13. Described more specifically, the control unit 20 generates the control signals based on the detection information of the external force as received from the force detecting portion 16. The control unit 20 is electrically connected to the force detecting portion 16 and the actuators 14 of the individual joints 13 of the arm portion 12, respectively, so that signals can be transmitted and received between them. The control unit 20 outputs the control signals, which correspond to the individual joints 13, to the actuators 14 of the individual joints 13, respectively, and actuates the individual joints 13 based on these control signals. The control unit 20 is also electrically connected to the first medical instrument 30 via the holding portion 11 and arm portion 12 so that signals can be transmitted and received between them. The control unit 20 outputs a control signal to the first medical instrument 30, and actuates the first medical instrument 30 based on this control signal.

The first medical instrument 30 is operated by the holding device 10, and has a first end effector 31. The first medical instrument 30 also has a distal end portion 32 or a first distal end portion, a proximal end portion 33 or a first proximal end portion, and an insertion portion 34 or a first insertion portion extending from the proximal end portion 33 to the distal end portion 32. The first end effector 31 is arranged on the distal end portion 32. The proximal end portion 33 is held on the holding portion 11 of the holding device 10. The insertion portion 34 is formed in an elongated slender structure. In the medical instrument 30, parts on a distal end side of the insertion portion 34, specifically the insertion portion 34 and the distal end portion 32 are those which have a possibility of being inserted into the body of a patient P.

In this embodiment, the first end effector 31 is a pair of grasping forceps. Using as a drive source an actuator (not depicted) included in the first medical instrument 30, the first end effector 31 is opened and closed by a drive mechanism that uses an operation wire or the like (not depicted), and can grasp a tissue or the like in the body. The first end effector 31 performs opening and closing according to control signals outputted from the control unit 20.

The insertion portion 34 has a joint 35 on a distal end side thereof. Therefore, the insertion portion 34 has a proximal-side insertion portion 34A extending from the proximal end portion 33 to the joint 35, and a distal-side insertion portion 34B extending from the joint 35 to the distal end portion 32. The joint 35 is a joint that allows bending movement of a single degree of freedom. The distal-side insertion portion 34B can, therefore, be bent via the joint 35 in a predetermined direction relative to the proximal-side insertion portion 34A. Bending operation of the distal-side insertion portion 34B can be performed by a drive mechanism, which uses an operation wire or the like (undepicted), while employing as a drive source an actuator (not depicted) included in the first medical instrument 30. This bending operation of the distal-side insertion portion 34B is performed according to a control signal outputted from the control unit 20.

The second medical instrument 40 is grasped by the operator, and is used in procedures for the patient P. The second medical instrument 40 has a second end effector 41, and an operating portion 42 that operates the second end effector 41. The second medical instrument 40 also has a distal end portion 43, a proximal end portion 44, and an insertion portion 45 extending from the proximal end portion 44 to the distal end portion 43. The second end effector 41 is arranged on the distal end portion 43. The operating portion 42 is disposed on the proximal end portion 44. The insertion portion 45 is formed in an elongated slender structure.

In this embodiment, the second end effector 41 is a pair of grasping forceps. The operating portion 42 can open and close the second end effector 41 by a drive mechanism that uses an operation wire or the like (not depicted). The second end effector 41 can, therefore, grasp the first medical instrument 30 or a tissue or the like in the body.

In addition, the medical system 1 further includes a main operating portion 50, an observation device 51, and a monitor 54.

The main operating portion 50 is configured to enable operation of the first medical instrument 30 held by the arm portion 12 and holding portion 11 of the holding device 10. The main operating portion 50 is electrically connected to the control unit 20 so that signals can be transmitted to and received from the control unit 20. Based on an input from the main operating portion 50, the control unit 20 generates control signals to be used to actuate the first medical instrument 30 held on the arm portion 12 and holding portion 11, and transmits the control signals to the arm portion 12. Based on the transmitted control signals, the individual joints 13 of the arm portion 12 and the first medical instrument 30 are actuated.

The observation device 51 has an observation portion 52, such as a laparoscope, that can perform observations inside the body of the patient P, and an observation arm portion 53 to which the observation portion 52 is attached. The observation arm portion 53 has a plurality of joints so that the observation portion 52 can be moved to a desired position. The observation portion 52 and observation arm portion 53 are electrically connected to the control unit 20 so that signals can be transmitted to and received from the control unit 20, and therefore can be operated by the main operating portion 50.

The monitor 54 is, for example, a liquid crystal display, and is electrically connected to the control unit 20. The monitor 54 displays an internal image of the patient P as acquired by the observation portion 52.

The control unit 20 has a first mode and a second mode as control modes that control the arm portion 12 of the holding device 10 and the first medical instrument 30. The first mode is a control mode that can move the arm portion 12 and first medical instrument 30 by the main operating portion 50. The second mode is a control mode that can move the arm portion 12 and the first medical instrument 30 by an external force applied to the first medical instrument 30. In the first mode, neither the arm portion 12 nor the first medical instrument 30 can be moved by an external force applied to the first medical instrument 30. In the second mode, neither the arm portion 12 nor the first medical instrument 30 can be moved by the main operating portion 50. These control modes can be switched, for example, by a foot switch 55 electrically connected to the control unit 20.

About operation during use of the medical system 1 according to this embodiment, a description will next be made using an example in which an operator Op pulls a tissue T in an abdominal cavity Ac of the patient P during a procedure.

As depicted in FIG. 2, the first medical instrument 30 is held on the holding portion 11 of the holding device 10. In the first medical instrument 30, the parts on the distal end side of the insertion portion 34 are inserted in the abdominal cavity Ac through a port Ap1 formed in an abdominal wall Aw of the patient P. The first end effector 31 of the first medical instrument 30 has grasped the tissue T in the abdominal cavity Ac, and is pulling the tissue T upward.

The pulling operation by the first medical instrument 30 is performed through operation of the main operating portion 50 by an assistant to the operator Op. Therefore, the control mode of the control unit 20 is set in the first mode. The control unit 20 also sets the position of the port Ap1 as a remote center Rc. Therefore, the control unit 20 actuates the individual joints 13 of the arm portion 12 so that a part of the first medical instrument 30 always exists at the remote center Rc irrespective of the position and posture of the first medical instrument 30.

The second medical instrument 40 is grasped by the operator Op. In the second medical instrument 40, a part on a distal end side of the insertion portion 45 is inserted in the abdominal cavity Ac through a port Ap2 formed in the abdominal wall Aw of the patient P.

Although not depicted in FIG. 2, conditions in the abdominal cavity Ac can be observed by the observation portion 52 inserted in the abdominal cavity Ac through an undepicted port formed in the abdominal wall Aw. A trocar may be disposed in each port formed in the abdominal wall Aw.

There is now described a procedure through which the operator Op moves the first medical instrument 30 to a desired position under the circumstances described hereinbefore. FIG. 3 is a flow chart illustrating operation of the medical system 1.

As illustrated in FIG. 3, the operator Op operates the foot switch 55 to switch the control mode of the control unit 20 from the first mode to the second mode in step S1. As a consequence, the arm portion 12 and first medical instrument 30 can be moved by an external force applied to the first medical instrument 30.

The operator Op operates the second medical instrument 40 so that the insertion portion 34 of the first medical instrument 30 in the abdominal cavity Ac is grasped by the second end effector 41. With the insertion portion 34 grasped by the second end effector 41, an external force F1 is applied to the first medical instrument 30 to move the first end effector 31, which is grasping the tissue T, in a desired direction in step S2.

In step S3, the force detecting portion 16 detects the external force F1 applied to the first medical instrument 30. The force detecting portion 16 outputs the detected external force F1 as detection information of the external force F1 to the control unit 20 in step S4.

In step S5, the control unit 20 receives the detection information of the external force F1 from the force detecting portion 16, and based on the external force F1 detected by the force detecting portion 16, generates control signals to actuate the individual joints 13 of the arm portion 12. At this time, the control unit 20 performs so-called copying control. Described more specifically, the control unit 20, based on detection information including the magnitude and direction of the external force F1, generates control signals to actuate the individual joints 13, so that the external force F1 applied to the first medical instrument 30 is cancelled out. In other words, the control unit 20 generates control signals to actuate the individual joints 13 so that the first medical instrument 30 is moved according to the magnitude of the external force F1, which has been applied to the first medical instrument 30, in the direction of the external force F1.

The control unit 20 outputs the generated control signals to the individual joints 13 in step S6, and actuates the individual joints 13 based on the control signals in step S7. As the movement of the first medical instrument 30 is restrained at the remote center Rc as described hereinbefore, the individual joints 13 move so that a part of the first medical instrument 30 always exists at the remote center Rc.

Until the end effector 31 moves to a desired position, the external force F1 is continuously applied by the second medical instrument 40 to the first medical instrument 30 in step S8. If the first end effector 31 has moved to the desired position, the second end effector 41 is opened to release the first medial instrument 30 from the second end effector 41 in step S9. The foot switch 55 is then operated to switch the control mode of the control unit 20 from the second mode to the first mode in step S10. As a consequence, the arm portion 12 and the first medical instrument 30 are prevented from moving under an external force applied unintentionally.

The holding device 10 in this embodiment includes the holding portion 11 configured to hold the first medical instrument 30 having the first end effector 31, the arm portion 12 having the joints 13 and the distal end portion 12a connected to the holding portion 11, the base portion 15 connected to the proximal end portion 12b of the arm portion 12, the force detecting portion 16 configured to detect the external force F1 applied to the first medical instrument 30 which is held on the holding portion 11, and the control unit 20 configured to generate, based on the external force F1 detected by the force detecting portion 16, control signals to actuate the joints 13.

According to the configuration described hereinbefore, the control unit 20, based on an external force applied to the first medical instrument 30, generates control signals to actuate the joints 13, so that the application of the external force F1 to the first medical instrument 30 can actuate the individual joints 13 according to the external force F1. Through the actuation of the joints 13, it is possible to move the first medical instrument 30 held on the holding portion 11 which is connected to the arm portion 12 having the joints 13. The first medical instrument 30 can, therefore, be easily moved to the desired position by simply applying the external force F1 to the first medical instrument 30.

On the other hand, the first medical instrument 30 has the distal end portion 32 with the first end effector 31 arranged thereon, the proximal end portion 33 held on the holding portion 11, and the insertion portion 34 extending from the proximal end portion 33 to the distal end portion 32. The force detecting portion 16 detects the external force F1 applied to the insertion portion 34 or the distal end portion 32.

According to the configuration described hereinbefore, the force detecting portion 16 detects the external force F1 which is applied to the insertion portion 34 or distal end portion 32 and which has a possibility of being inserted into the body during the procedure. It is, accordingly, possible to prevent the joints 13 from being moved by an external force applied to an unintended position.

The medical system 1 according to this embodiment includes the first medical instrument 30 having the first end effector 31, the second medical instrument 40 having the second end effector 41, and the holding device 10. The holding device 10 has the holding portion 11 configured to hold the first medical instrument 30, the arm portion 12 having the joints 13 and the distal end portion 12a connected to the holding portion 11, the base portion 15 connected to the proximal end portion 12b of the arm portion 12, the force detecting portion 16 configured to detect the external force F1 applied to the first medical instrument 30 which is held on the holding portion 11, and the control unit 20 configured to generate, based on the external force F1 detected by the force detecting portion 16, control signals to actuate the joints 13.

According to the configuration described hereinbefore, the application of the external force F1 to the first medical instrument 30 can actuate the individual joints 13 according to the external force F1. As the first medical instrument 30 is connected to the joints 13 via the holding portion 11, the first medical instrument 30 can be easily moved to a desired position by simply applying the external force F1 to the first medical instrument 30.

An operating method of the holding device 10 in this embodiment, the holding device 10 including the holding portion 11 with the first medical instrument 30 held thereon, the arm portion 12 having the joints 13 and the control unit 20 configured to generate control signals to actuate the joints 13, includes step S3 of detecting the external force F1 applied to the first medical instrument 30, step S5 of generating control signals based on the detected external force F1, and step S7 of actuating the joints 13 based on the control signals.

According to the operating method described hereinbefore, the application of the external force F1 to the first medical instrument 30 can actuate the individual joints 13 according to the external force F1. As the first medical instrument 30 is connected to the joints 13 via the holding portion 11, the first medical instrument 30 can be easily moved to a desired position by simply applying the external force F1 to the first medical instrument 30.

An operating method of the medical system 1 according to this embodiment, the medical system 1 including the first medical instrument 30, the second medical instrument 40, and the holding device 10 having the holding portion 11 with the first medical instrument 30 held thereon, the arm portion 12 having the joints 13 and the control unit 20 configured to generate control signals to actuate the joints 13, includes step S3 of detecting the external force F1 applied to the first medical instrument 30 by the second medical instrument 40, step S5 of generating control signals based on the detected external force F1, and step S7 of actuating the joints 13 based on the control signals.

According to the operating method described hereinbefore, the application of the external force F1 to the first medical instrument 30 by the second medical instrument 40 can actuate the individual joints 13 according to the external force F1. As the first medical instrument 30 is connected to the joints 13 via the holding portion 11, the first medical instrument 30 can be easily moved to a desired position by simply applying the external force F1 to the first medical instrument 30 from the second medical instrument 40.

In this embodiment, the first end effector 31 of the first medical instrument 30 has been described to be the grasping forceps. However, the first end effector 31 is not limited to such grasping forceps, and the configuration of the first end effector 31 may be changed as needed according to the details or the like of the procedure. For example, the end effector 31 may be a retractor that excludes a tissue in the body, or may be another auxiliary instrument.

Further, the insertion portion 34 of the first medical instrument 30 has been described to have the joint 35. However, the insertion portion 34 is not limited to having such a joint, and the configuration of the insertion portion 34 may be changed as needed according to the details or the like of the procedure. For example, the insertion portion 34 may have a plurality of joints, or may have no joint.

The second end effector 41 of the second medical instrument 40 has been described to be the grasping forceps. However, the second end effector 41 is not limited to such grasping forceps, and the configuration of the second end effector 41 may be changed as needed according to the details or the like of the procedure. Further, no particular limitation is imposed on the second end effector 41 insofar as it has a configuration that enables to apply an external force to the first medical instrument 30. The second end effector 41 may apply an external force to the first medical instrument 30 through its contact to the first medical instrument 30, for example, by pushing or otherwise moving the first medical instrument 30.

The medical system 1 has been described to include the single arm portion 12. According to the details or the like of the procedure, a plurality of arm portions 12 may be included.

The computing unit 18 has been described to be arranged independently of the control unit 20. However, the computing unit 18 may be configured as a part of the control unit 20.

The control unit 20 may perform control so that a force equal to or greater than a preset value is not applied to the tissue T upon actuation of the individual joints 13 by the external force F1 applied to the first medical instrument 30.

Second Embodiment

Figure 4:
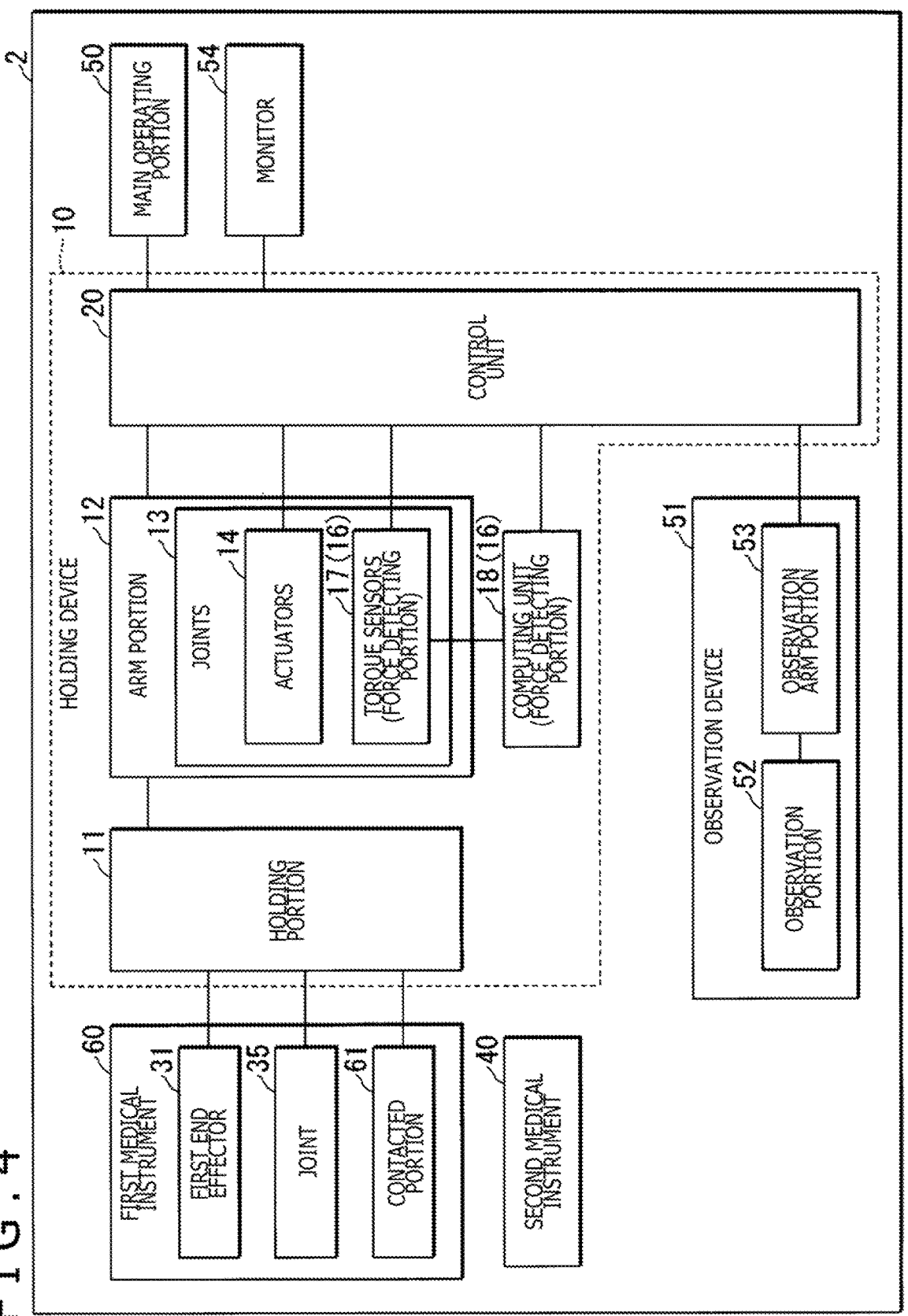
FIG. 4 is a functional block diagram of a medical system according to a second embodiment of the present disclosure.
Figure 5:
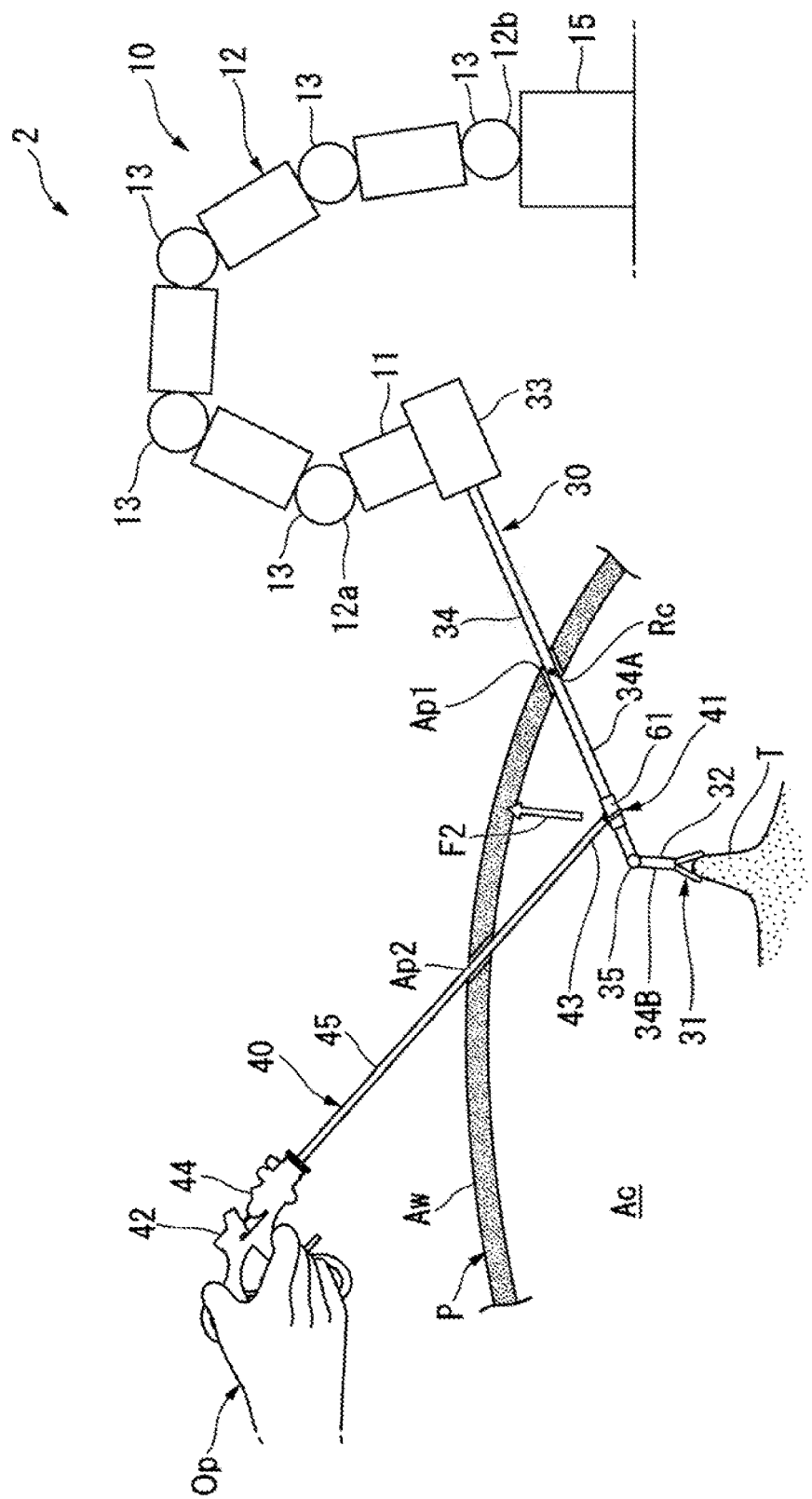
FIG. 5 is a view schematically depicting the medical system according to the second embodiment.

With reference to FIGS. 4 and 5, a description will next be made about a second embodiment of the present disclosure.

FIG. 4 is a functional block diagram of a medical system 2 according to the second embodiment. FIG. 5 is a view schematically depicting the medical system 2.

As depicted in FIGS. 4 and 5, the medical system 2 is different from the medical system 1 according to the first embodiment in that the first medical instrument 60 further includes a contacted portion 61. It is to be noted that a detailed description is omitted herein about elements having similar configurations as in the medical system 1 according to the first embodiment.

The first medical instrument 60 further includes the contacted portion 61 in addition to the first end effector 31. The contacted portion 61 is disposed on a distal end side of the proximal-side insertion portion 34A. Described more specifically, the contacted portion 61 is disposed in the vicinity of the joint 35 on the proximal-side insertion portion 34A, in other words, at a position closer to the joint 35 than the proximal end portion 33 on the proximal-side insertion portion 34A, and on an outer circumferential wall of the proximal-side insertion portion 34A. The contacted portion 61 is configured of a contact sensor, and detects its grasping by the second end effector 41 of the second medical instrument 40. The contacted portion 61 is electrically connected to the control unit 20 via the holding portion 11 and arm portion 12 so that signals can be transmitted to and received from the control unit 20.

The contacted portion 61 has the function of the foot switch 55 in the first embodiment. Described specifically, the control unit 20 switches the control mode from the first mode to the second mode if the contacted portion 61 has detected contact, for example, as a result of grasping or the like of the contacted portion 61 by the second end effector 41. The control unit 20 maintains the second mode while the detection of the contact by the contacted portion 61 continues. If the contacted portion 61 no longer detects contact, the control unit 20 switches the control mode from the second mode to the first mode. The control unit 20 maintains the first mode until the contacted portion 61 detects contact.

If an operator Op is desired to move the first medical instrument 60 by the second medical instrument 40 in the medical system 2, the operator Op grasps the contacted portion 61 of the first medical instrument 60 by the second end effector 41. As a consequence, the control mode of the control unit 20 is switched to the second mode so that the first medical instrument 60 can be moved by an external force applied to the first medical instrument 60. With the contacted portion 61 of the first medical instrument 60 grasped by the second end effector 41, the operator Op moves the first medical instrument 60 to a desired position in a similar manner as in the first embodiment. By releasing the contacted portion 61 from the second end effector 41, the control mode is switched from the second mode to the first mode.

According to the configuration described hereinbefore, the joints 13 of the arm portion 12 are actuated by the external force F2 applied to the first medical instrument 60 only when the contacted portion 61 has detected contact by the second end effector 41. It is, therefore, possible to prevent the joints 13 from moving by contact of an internal organ or the like to a position other than the contacted portion 61 in the first medical instrument 60.

In this embodiment, the contacted portion 61 is disposed on the distal end side of the proximal-side insertion portion 34A, but is not limited to such a position. The contacted portion 61 may be disposed on the insertion portion 34 or the distal end portion 32. Further, a plurality of contacted portions 61 may also be disposed.

Figure 6:
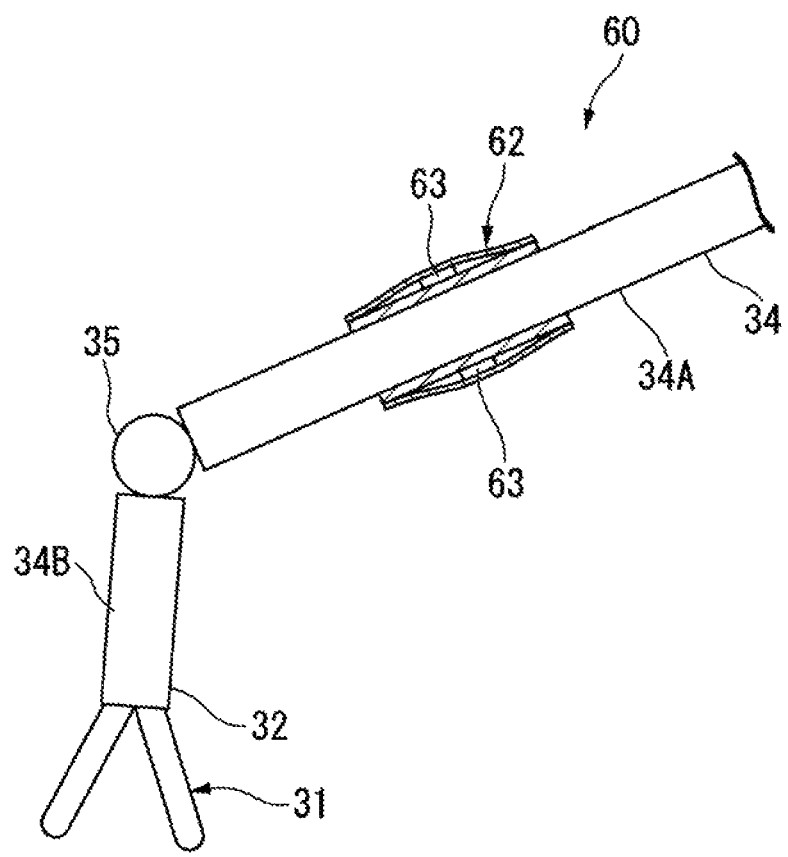
FIG. 6 is a view depicting an example of the configuration of a contacted portion in the medical system according to the second embodiment.

To reduce false detections at the contacted portion 61, the first medical instrument 60 may have a contacted portion 62 depicted in FIG. 6. FIG. 6 is a view depicting the configuration of the contacted portion 62.

The contacted portion 62 includes a pair of contact sensors 63 or contact detecting portions. The paired contact sensors 63 detect a contacted state at the contacted portion 62. In this example, the paired contact sensors 63 are arranged on the outer circumferential wall of the proximal-side insertion portion 34A at positions opposing each other with a longitudinal axis of the proximal-side insertion portion 34A interposed therebetween. If both the contact sensors 63 have detected contact by the second end effector 41, the control unit 20 determines that the contacted portion 62 has detected the contact.

In this case, the control unit 20, based on the contacted state at the contacted portion 62 and the external force F2, generates control signals to actuate the joints 13. Described specifically, if the paired contact sensors 63 have detected contact, the control unit 20, based on the external force F2 detected at the force detecting portion 16, generates control signals to actuate the joints 13. If the paired contact sensors 63 have detected no contact, on the other hand, the control unit 20 generates control signals to maintain the joints 13 at and in the same positions and postures, respectively.

According to the configuration described hereinbefore, only when both the contact sensors 63 have detected contact by the second end effector 41, the joints 13 of the arm portion 12 can be actuated by the external force F2 applied to the first medical instrument 60. It is, therefore, possible to reduce false detections by such a case that an internal organ comes to contact with the contacted portion 62.

An operating method of the medical system 2, the operating method corresponding to the configuration described hereinbefore, further includes a step of detecting a contacted state by the second medical instrument 40 at the first medical instrument 30 in the hereinbefore-described operating method of the medical system 1. In step S5 that generates control signals, the control signals are generated based on the contacted state and the external force F2.

Modification

Figure 7:
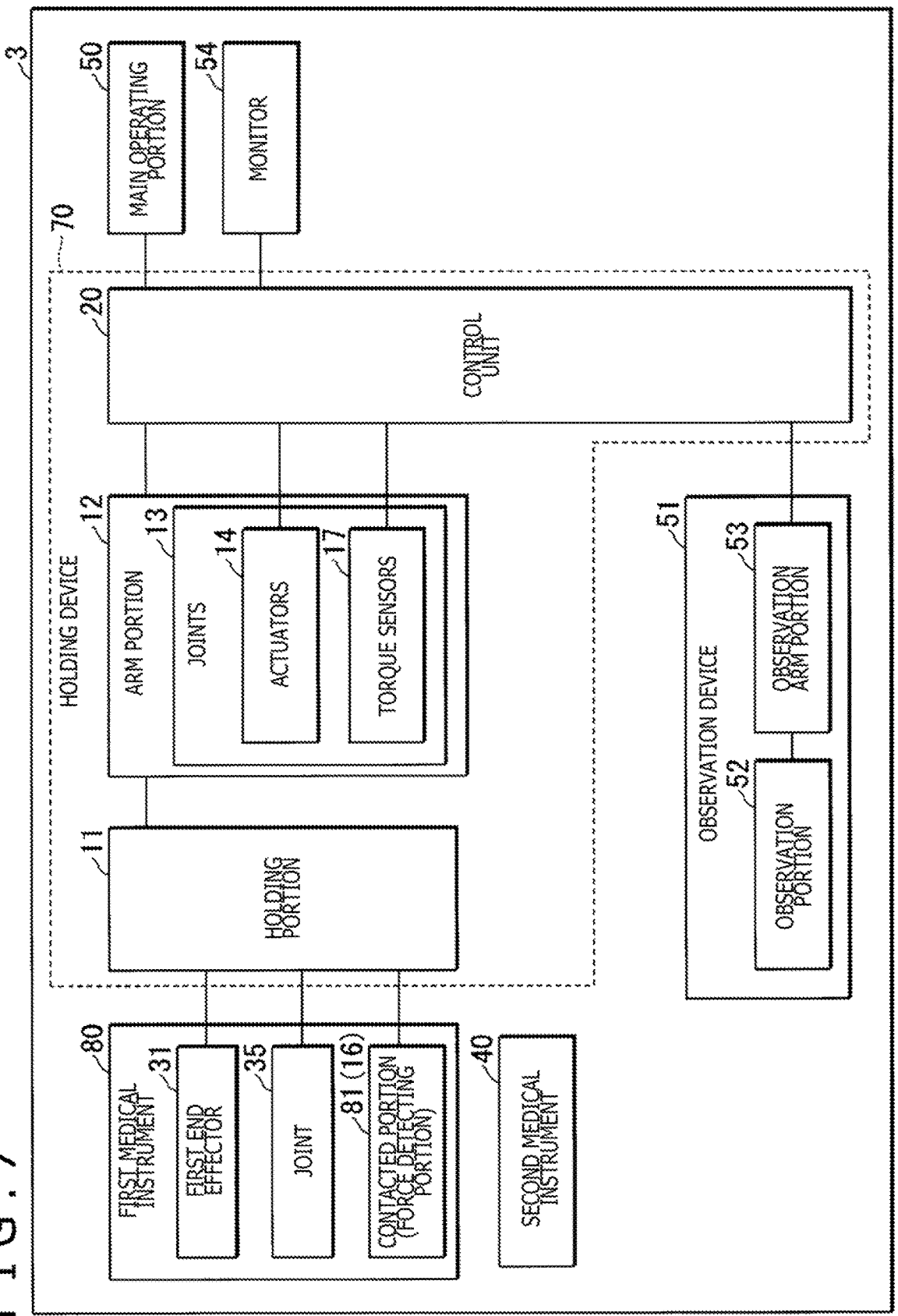
FIG. 7 is a functional block diagram of a modification of the medical system according to the second embodiment.

In FIG. 7, a modification of the medical system 2 according to the second embodiment is depicted. FIG. 7 is a functional block diagram of a medical system 3 according to this modification.

As depicted in FIG. 7, the medical system 3 is different from the hereinbefore-described medical system 2 in that a contacted portion 81 of a first medical instrument 80 is configured to enable detection of an external force. It is to be noted that a detailed description is omitted herein about elements having similar configurations as in the medical system 2.

The contacted portion 81 is configured to enable detection of an external force applied to the contacted portion 81. Described specifically, the contacted portion 81 is configured having a force sensor in addition to the contact sensors described hereinbefore. To the force sensor, a configuration can be applied. The force sensor may be, for example, a strain gauge.

By the configuration described hereinbefore, the contacted portion 81 can function as the force detecting portion 16. In the medical system 3, therefore, the torque sensor 17 in a holding device 70 does not function as a force detecting portion, and the holding device 70 does not include the computing unit 18.

In the medical system 3, the contacted portion 81 detects only an external force directly applied to the contacted portion 81, and outputs detection information of the external force to the control unit 20. As appreciated from the foregoing, the force detecting portion may be arranged in the first medical instrument 80 to be inserted into the body.

Third Embodiment

Figure 8:
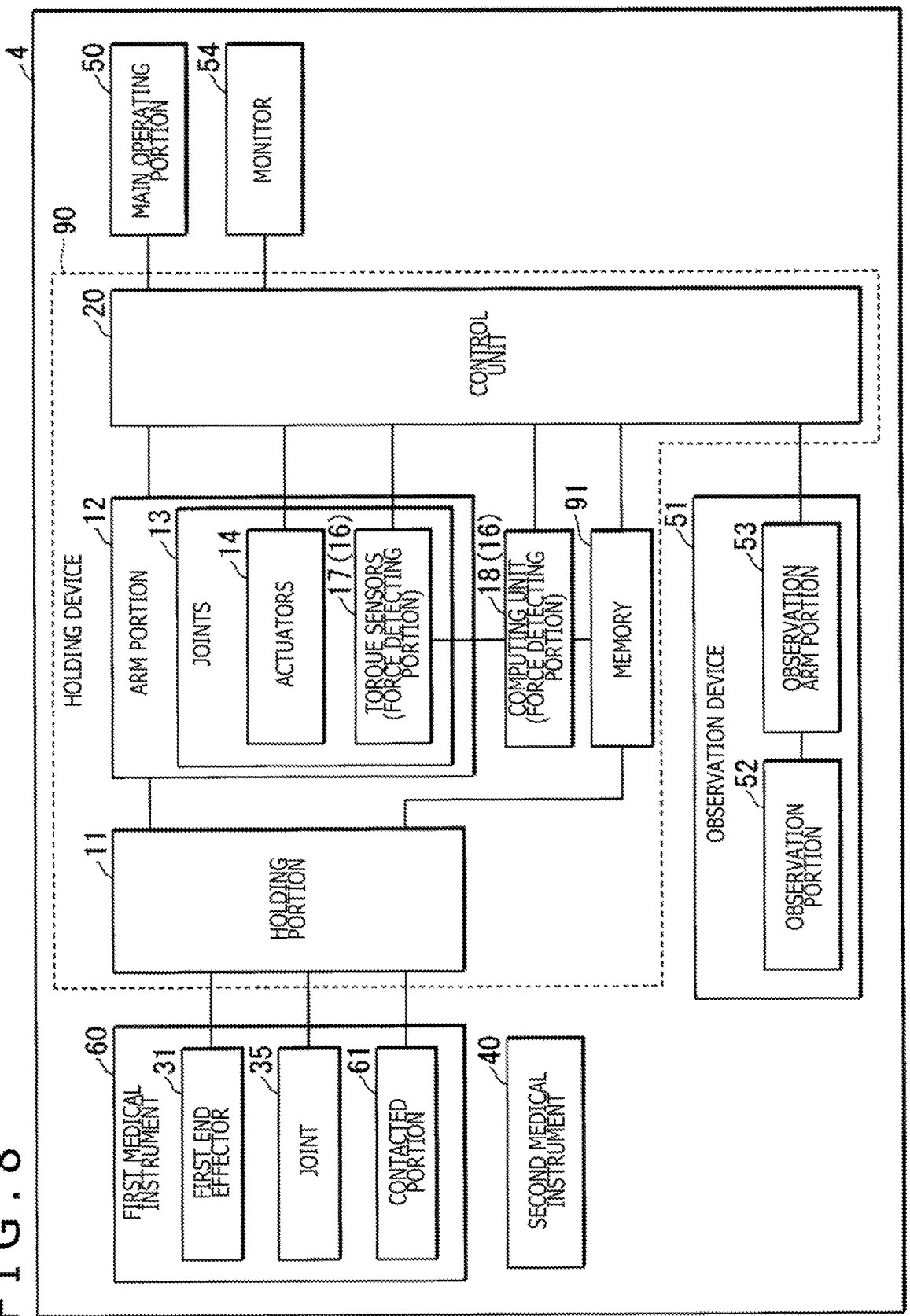
FIG. 8 is a functional block diagram of a medical system according to a third embodiment of the present disclosure.

With reference to FIG. 8, a description will next be made about a third embodiment of the present disclosure.

FIG. 8 is a functional block diagram of the medical system 4 according to the third embodiment. The medical system 4 is different from the medical system 2 according to the second embodiment in that a holding device 90 further includes a memory 91. It is to be noted that a detailed description is omitted herein about elements having similar configurations as in the medical system 2 according to the second embodiment.

The memory 91 is a storage device from and in which reading and writing are possible from the control unit 20 or the like. The memory 91 is electrically connected to each of the control unit 20, force detecting portion 16 and contacted portion 61. The force detecting portion 16 outputs detection information of an external force at predetermined intervals to the memory 91. The memory 91 can store detection information of external forces outputted from the force detecting portion 16. The contacted portion 61 outputs contact detection information, which indicates whether or not a contact has been detected, at predetermined intervals to the memory 91. The memory 91 can store the contact detection information outputted from the contacted portion 61. The control unit 20 can read the detection information of external forces and the contact detection information stored in the memory 91 as needed.

The control unit 20 also includes a third mode as an additional control mode. The third mode is a control mode that can maintain the state, in which the arm portion 12 and first medical instrument 60 have been actuated by an external force applied to the first medical instrument 60, even after the application of the external force is stopped. The control mode can be switched to the third mode, for example, by an undepicted foot switch.

Described specifically, in the third mode, if the contacted portion 61 of the first medical instrument 60 has been grasped by the second end effector 41, the contacted portion 61 outputs first contact detection information, which indicates detection of a contact, to the memory 91 and control unit 20. The memory 91 stores the received first contact detection information. The contacted portion 61 continues to output the first contact detection information at predetermined intervals to the memory 91 and control unit 20 while the contact is continuously detected.

If the second end effector 41 applies an external force to the first medical instrument 60 with the contacted portion 61 being kept grasped, the first medical instrument 60 moves according to the applied external force as in the second mode. While the second end effector 41 is continuously grasping the contacted portion 61, the force detecting portion 16 outputs detection information of the external force applied to the first medical instrument 60, the detection information including a case that the magnitude of the external force is 0, at predetermined intervals to the memory 91 and control unit 20. The memory 91 stores the received detection information of the external force.

Here, if the application of the external force to the first medical instrument 60 is stopped and the second end effector 41 is released from the contacted portion 61, the force detecting portion 16 no longer detects the external force because of the separation of the second end effector 41 from the first medical instrument 60. In this case, the contacted portion 61 outputs second contact detection information, which indicates that no contact has been detected, to the memory 91 and control unit 20. At the same time, the force detecting portion 16 stops outputting the detection information of the external force to the memory 91 and control unit 20.

In this case, the control unit 20 retrieves detection information, which allows to determine that the magnitude of the external force contained in the detection information is not 0, in other words, is greater than 0, through the detection information of external forces as stored in the memory 91 from the reception of the latest first contact detection information until before the reception of the second contact detection information. From the memory 91, the control unit 20 reads the detection information, which is closest to a clock time at which the second contact information was received, among the retrieved detection information. The control unit 20 generates control signals to be used for actuating the individual joints 13 such that a force having the same magnitude and direction as the external force contained in the read detection information is applied to the contacted portion 61 of the first medical instrument 60, and outputs the control signals to the individual joints 13. The individual joints 13 are actuated based on the received control signals. The individual joints 13 continue to be actuated based on the received control signals until the control mode of the control unit 20 is switched from the third mode to another mode. A switch or the like may also be included in the medical system 4 to stop the actuation of the individual joints 13.

In the third mode described hereinbefore, even after an external force applied to the contacted portion 61 by the second end effector 41 is eliminated while a tissue T grasped by the first end effector 31 of the first medical instrument 60 is being pulled upward, for example, as depicted in FIG. 5, the tissue T can be continuously pulled under a force having the same magnitude and direction as the external force so that the pulling force can be maintained constant.

In the medical system 4, the hereinbefore-described contacted portion 62 may be disposed in place of the contacted portion 61. The contacted portion 62 includes the paired contact sensors 63, and therefore can detect, with high accuracy, a contacted state at the contacted portion 62.

In this case, if the second end effector 41 grasps the contacted portion 62 in the third mode, the paired contact sensors 63 detect that the second end effector 41 has come into contact with the contacted portion 62. If the second end effector 41 is released from the contacted portion 62 subsequent to application of an external force to the first medical instrument 60 by the second end effector 41 in the state described hereinbefore, the paired contact sensors 63 detect that the second end effector 41 is no longer in contact with the contacted portion 62. As a consequence, the contacted portion 62 outputs second contact detection information to the memory 91 and control unit 20, and at the same time the force detecting portion 16 stops outputting the detection information of the external force to the memory 91 and control unit 20.

Here, the control unit 20 reads, from the memory 91, the detection information of the external force which the force detecting portion 16 detected a predetermined period of time before the time at which the paired contact sensors 63 have detected that the second end effector 41 is no longer in contact with the contacted portion 62, in other words, the time at which the control unit 20 has received the second contact detection information. The control unit 20 generates control signals to actuate the individual joints 13 so that a force having the same magnitude and direction as the external force as contained in the read detection information is applied to the contacted portion 62 of the first medical instrument 60. In other words, the control unit 20 generates control signals to maintain a force having the same magnitude and direction as the external force that the force detecting portion 16 had detected the predetermined period of time ago.

Even after the external force applied to the contacted portion 62 by the second end effector 41 has been eliminated, the configuration described hereinbefore can also continuously pull the tissue T under the force having the same magnitude and direction as the external force so that the pulling force can be maintained constant.

Modification

Figure 9:
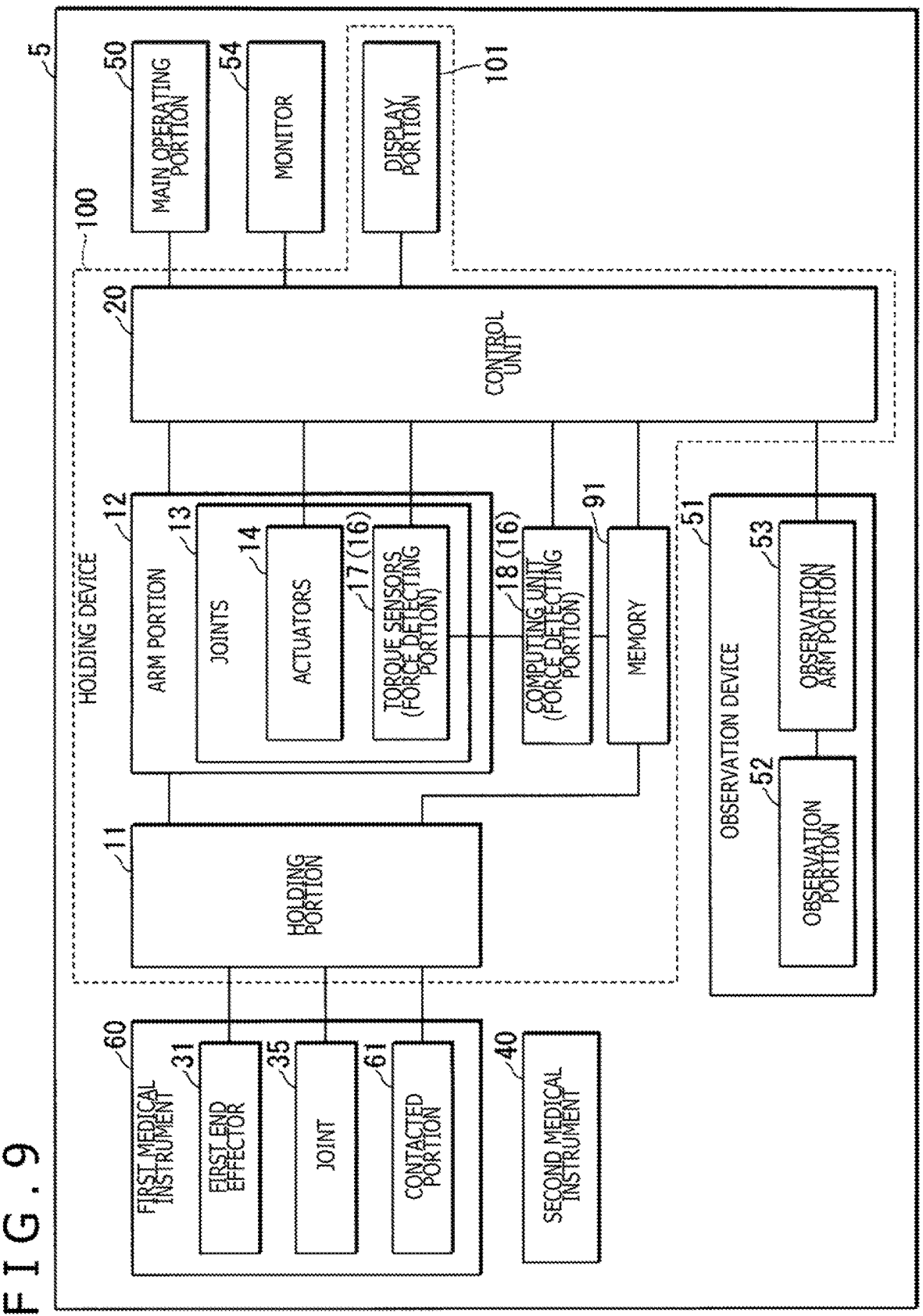
FIG. 9 is a functional block diagram of a modification of the medical system according to the third embodiment.

In FIG. 9, a modification of the medical system 4 according to this embodiment is depicted. FIG. 9 is a functional block diagram of a medical system 5 according to this modification.

As depicted in FIG. 9, the medical system 5 is different from the hereinbefore-described medical system 4 in that a holding device 100 further includes a display unit 101. It is to be noted that a detailed description is omitted herein about elements having similar configurations as in the medical system 4.

The display unit 101 is configured to enable display of information for an operator Op and an assistant, and may be, for example, a liquid crystal display or the like. The display unit 101 is electrically connected to the control unit 20. According to signals from the control unit 20, the magnitude and direction of the external force, which are contained in the detection information of the external force, are displayed on the display unit 101. The control unit 20 may generate signals such that the hereinbefore-described contact detection information may also be displayed on the monitor unit 101 in addition to the magnitude and direction of the external force as contained in the detection information of the external force.

By the configuration described hereinbefore, the operator Op can quantitively grasp the magnitude and direction of the external force applied to the first medical instrument 60.

In the medical system 5, the display unit 101 is arranged independently of the monitor 54. As an alternative, the monitor 54 may also have the function of the display unit 101.

The second embodiment has been described by taking, as an example, the case that the first medical instrument 60 has the contacted portion 61. However, the second embodiment is not limited to this configuration. Even if the first medical instrument 60 does not have the contacted portion 61 like the first medical instrument 30 in the first embodiment, the first medical instrument 60 can still be moved as described hereinbefore.

In this case, if the control mode of the control unit 20 has been switched to the third mode, the force detecting portion 16 outputs detection information of the external force applied to the first medical instrument 60, the detection information including a case that the magnitude of the external force is 0, at predetermined intervals to the memory 91 and control unit 20. Based on the received detection information of the external force, the control unit 20 determines whether or not the magnitude of the external force is 0. If the magnitude of the external force has been determined to be 0 subsequent to continuation of detection information that the magnitude of the external force was determined not to be 0, in other words, to be greater than 0, the control unit 20 generates control signals based on the detection information, which was available immediately preceding the detection information that the magnitude of the external force has been determined to be 0 and which determined the magnitude of the external force to be greater than 0.

Even after the external force applied to the first medical instrument 60 by the second end effector 41 has been eliminated, the actuation of the individual joints 13 based on the control signals can continuously pull the tissue T under the force having the same magnitude and direction as the external force so that the pulling force can be maintained constant.

Fourth Embodiment

Figure 10:
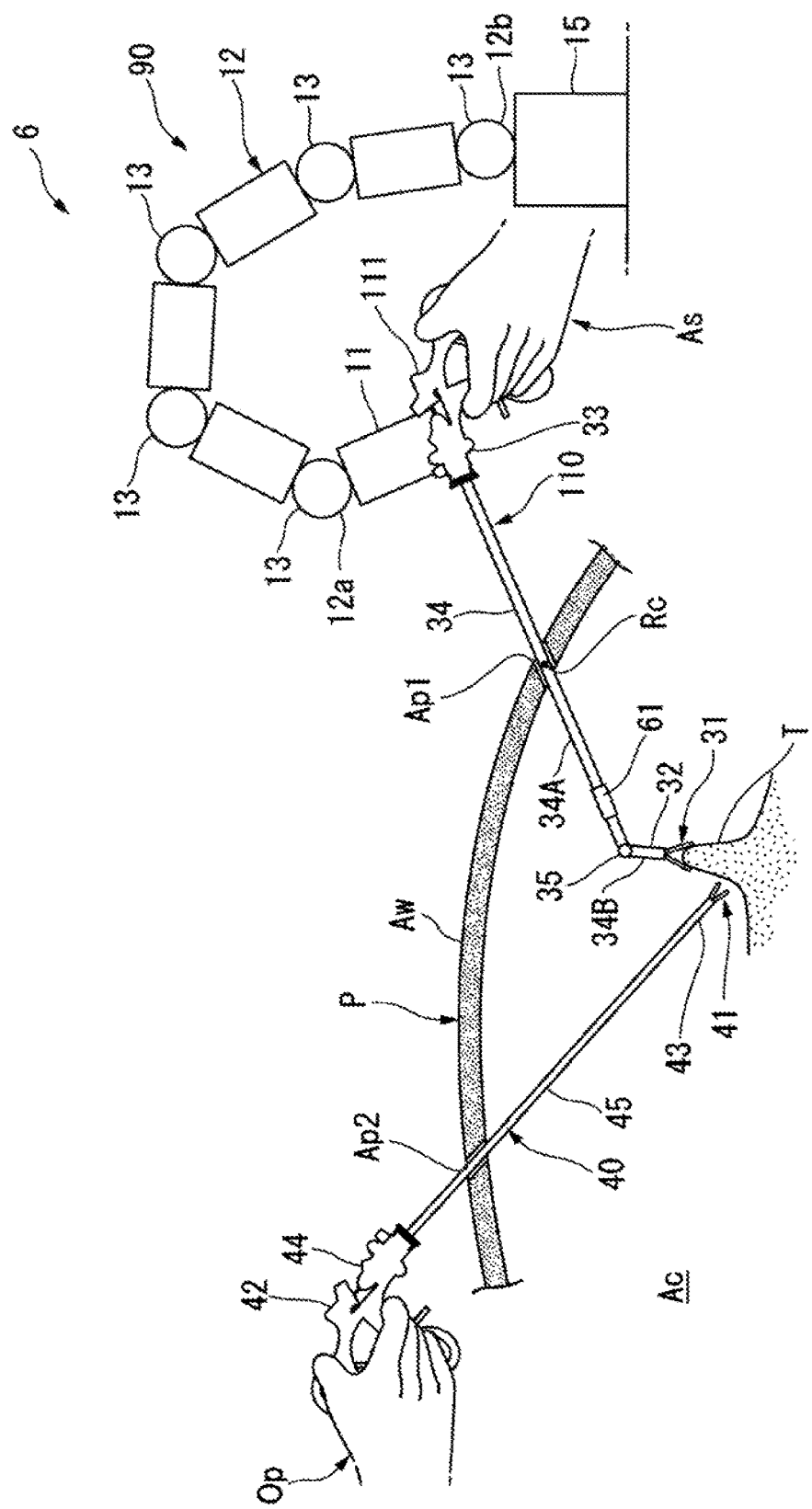
FIG. 10 is a view schematically depicting a medical system according to a fourth embodiment of the present disclosure.

With reference to FIG. 10, a description will next be made about a fourth embodiment of the present disclosure.

FIG. 10 is a view schematically depicting a medical system 6 according to the fourth embodiment. The medical system 6 is different from the medical system 4 according to the third embodiment in that the control unit 20 also includes a fourth mode as a further additional control mode. The medical system 6 includes the same functional blocks as the medical system 4 according to the third embodiment. It is to be noted that a detailed description is omitted herein about elements having similar configurations as in the medical system 4 according to the third embodiment.

The fourth mode is a control mode that, even after stopping application of an external force to a first medical instrument 110, still allows the first medical instrument 110 to move only in a direction in which the external force has been applied.

Described specifically, if the contacted portion 61 of the first medical instrument 110 has been grasped by the second end effector 41 in the fourth mode, the contacted portion 61 outputs first contact detection information, which indicates contact of the second end effector 41 to the contacted portion 61, to the memory 91 and control unit 20. The memory 91 stores the received first contact detection information. While the contact of the second end effector 41 to the contacted portion 61 is continuously detected, the contacted portion 61 continues to output the first contact detection information at predetermined intervals to the memory 91 and control unit 20.

If an external force is applied to the first medical instrument 110 with the contacted portion 61 grasped by the second end effector 41, the first medical instrument 110 moves according to the applied external force as in the second mode. While the second end effector 41 is continuously grasping the contacted portion 61, the force detecting portion 16 outputs detection information of the external force applied to the first medical instrument 110, the detection information including a case that the magnitude of the external force is 0, at predetermined intervals to the memory 91 and control unit 20. The memory 91 stores the received detection information of the external force.

If the application of the external force to the first medical instrument 110 is now stopped and the second effector 41 is released from the contacted portion 61, the contacted portion 61 outputs second contact detection information, which indicates that the contact to the contacted portion 61 by the second end effector 41 has not been detected, to the memory 91 and control unit 20. At the same time, the force detecting portion 16 stops outputting the detection information of the external force to the memory 91 and control unit 20.

In this case, the control unit 20 retrieves detection information, which allows to determine that the magnitude of the external force contained in the detection information is not 0, in other words, is greater than 0, through the detection information of external forces as stored in the memory 91 from the reception of the latest first contact detection information until before the reception of the second contact detection information. From the memory 91, the control unit 20 reads the detection information, which is closest to a clock time at which the second contact detection information was received, among the retrieved detection information. The control unit 20 controls so that the first medical instrument 110 can move only in the direction of the external force contained in the read detection information. At this time, the control unit 20 performs the hereinbefore-described copying control.

The first medical instrument 110 further includes an operating portion 111 in addition to the configuration of the first medical instrument 60. The operating portion 111 is disposed on the proximal end portion 33. It is to be noted that the operating portion 111 is disposed to facilitate for the assistant As to actuate the first medical instrument 110 directly and is not an essential element.

As the control unit 20 performs the hereinbefore-described control, the assistant As can move the first medical instrument 110 in the direction of the external force contained in the detection information read by the control unit 20 while grasping the operating portion 111 of the first medical instrument 110.

In the fourth mode described hereinbefore, even after an operator Op has eliminated an external force applied to the contacted portion 61 by the second end effector 41 while a tissue T grasped by the first end effector 31 of the first medical instrument 110 is being pulled upward, for example, as depicted in FIG. 10, the pulling force can be finely adjusted, with the pulling direction of the tissue T being restricted to the direction of the applied external force, through direct operation of the first medical instrument 110 by an assistant As.

Fifth Embodiment

Figure 11:
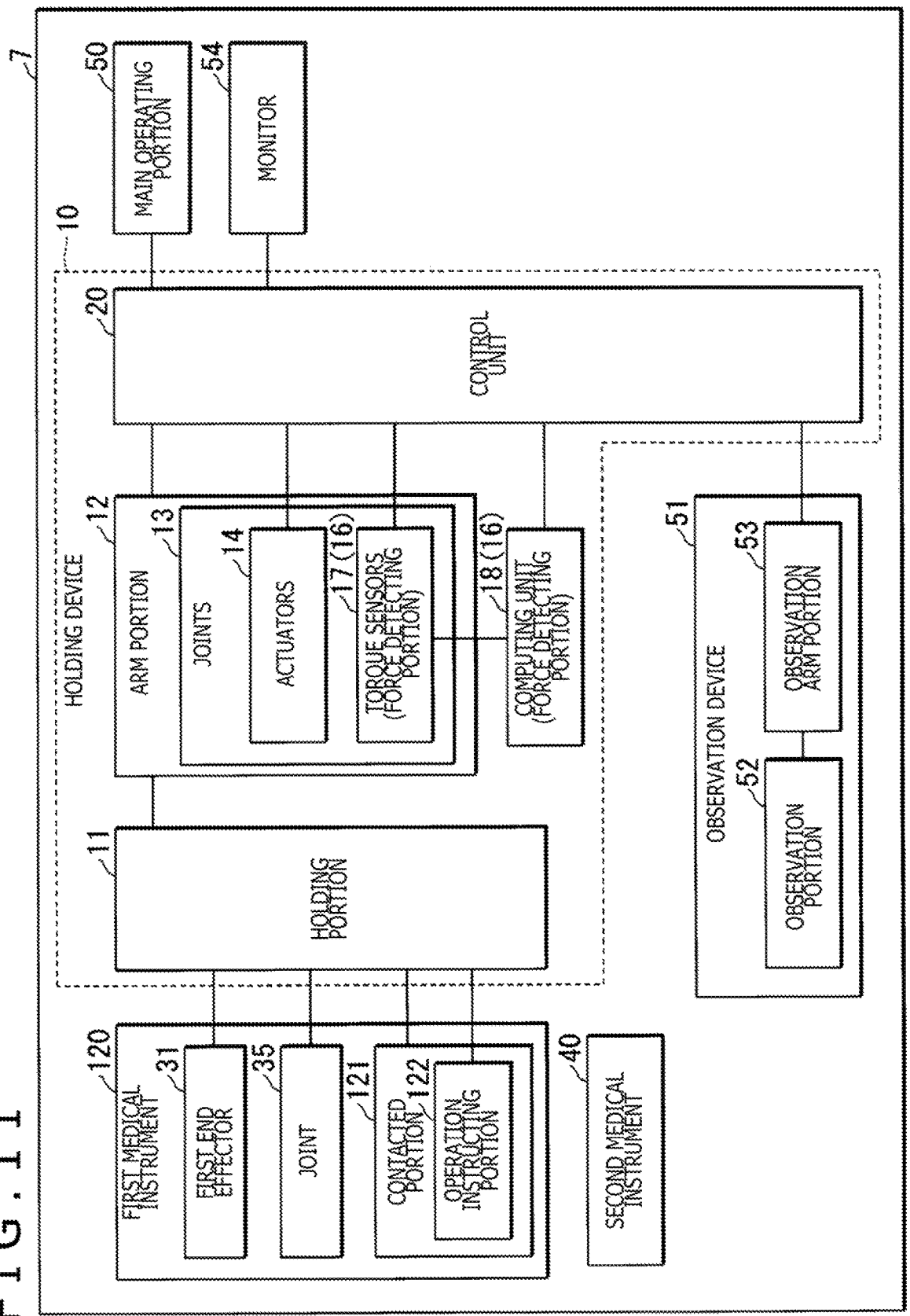
FIG. 11 is a functional block diagram of a medical system according to a fifth embodiment of the present disclosure.
Figure 12:
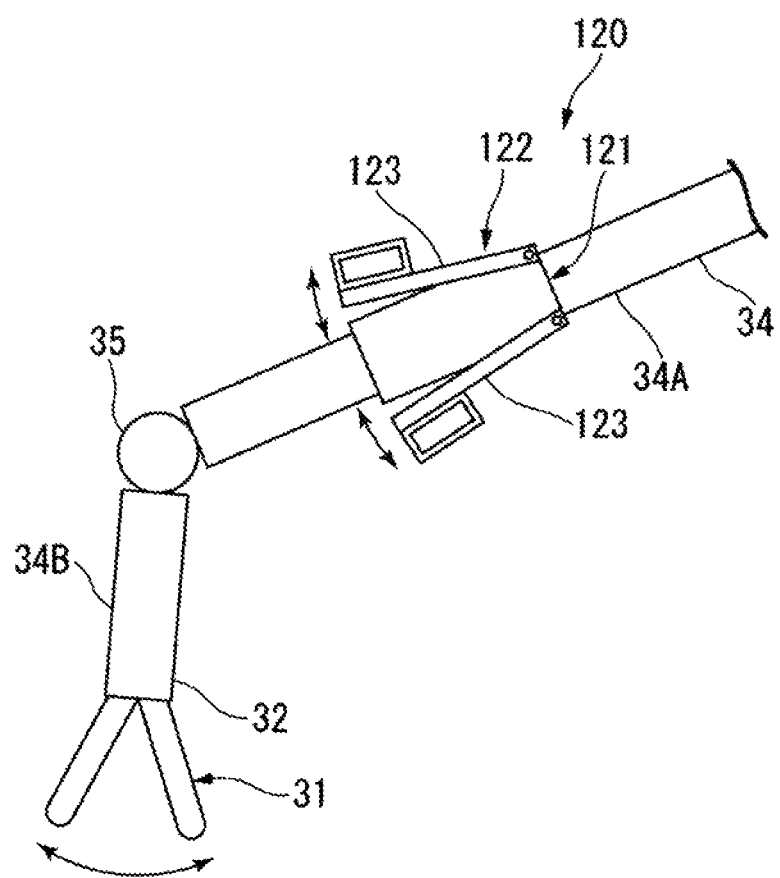
FIG. 12 is a view depicting on an enlarged scale a distal end side of a first medical instrument in the medical system according to the fifth embodiment.

With reference to FIGS. 11 and 12, a description will next be made about a fifth embodiment of the present disclosure.

FIG. 11 is a functional block diagram of a medical system 7 according to the fifth embodiment. FIG. 12 is a view depicting on an enlarged scale a distal end side of a first medical instrument 120 in the medical system 7.

As depicted in FIG. 11, the medical system 7 is different from the medical system 2 according to the second embodiment in that the first medical instrument 120 further includes an operation instructing portion 122. It is to be noted that a detailed description is omitted herein about elements having similar configurations as in the medical system 2 according to the second embodiment.

The first medical instrument 120 has a contacted portion 121. The contacted portion 121 is different from the contacted portion 61 in the first medical instrument 60 according to the second embodiment in that the contacted portion 121 has the operation instructing portion 122.

The operation instructing portion 122 is configured to enable operation of the first end effector 31. The operation instructing portion 122 is electrically connected to the control unit 20 so that signals can be transmitted and received therebetween. If the control mode of the control unit 20 is the second mode, operation signals are outputted to the control unit 20 by operation of the operation instructing portion 122. The control unit 20 generates, based on the operation signals, control signals to be used for actuating the first end effector 31, and outputs the control signals to the first end effector 31. The first end effector 31 performs opening and closing based on the control signals.

In FIG. 12, an example of the configuration of the operation instructing portion 122 is depicted. The operation instructing portion 122 has a pair of pivoted levers 123. The paired pivoted levers 123 are each connected pivotally to the contacted portion 121. The operation instructing portion 122 generates an operation signal corresponding to an opening angle between the paired pivoted levers 123. This opening angle can be adjusted by grasping the paired pivoted levers 123 with the second end effector 41 of the second medical instrument 40. As the control unit 20 generates the control signal based on the operation signal corresponding to the opening angle, the opening and closing of the first end effector 31 can controlled by the opening angle.

Owing to the configuration described hereinbefore, an operator Op can control movements of the first end effector 31 of the first medical instrument 120 by the second medical instrument 40 inside the body.

The configuration of the operation instructing portion 122 in this embodiment is merely illustrative, and the operation instructing portion 122 is not limited to the configuration. For example, the operation instructing portion 122 may include a force sensor, and may be configured so that the opening and closing of the first end effector 31 can be controlled according to the quantity of a force with which the operation instructing portion 122 is grasped by the second end effector 41.

Sixth Embodiment

Figure 13:
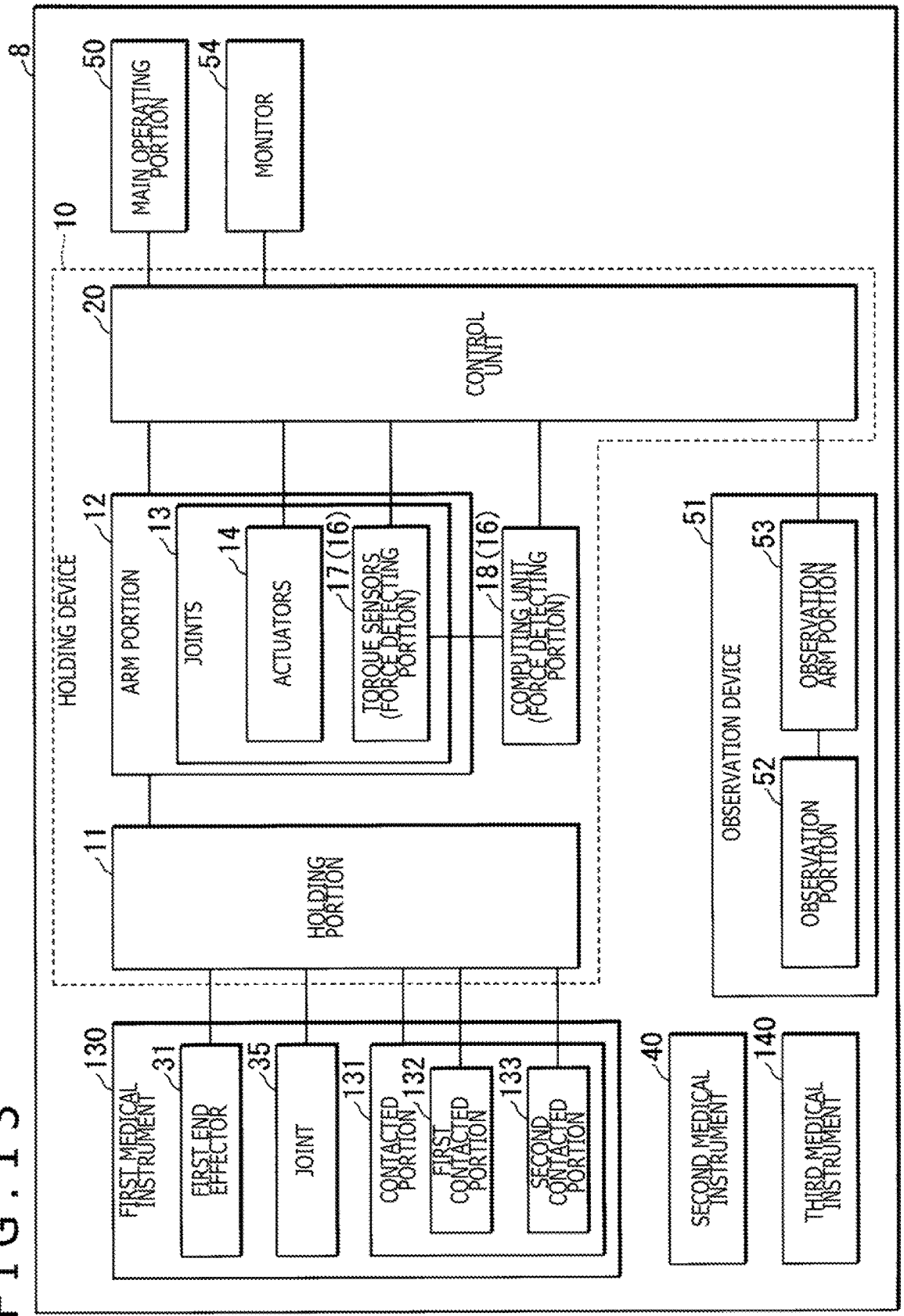
FIG. 13 is a functional block diagram of a medical system according to a sixth embodiment of the present disclosure.
Figure 14:
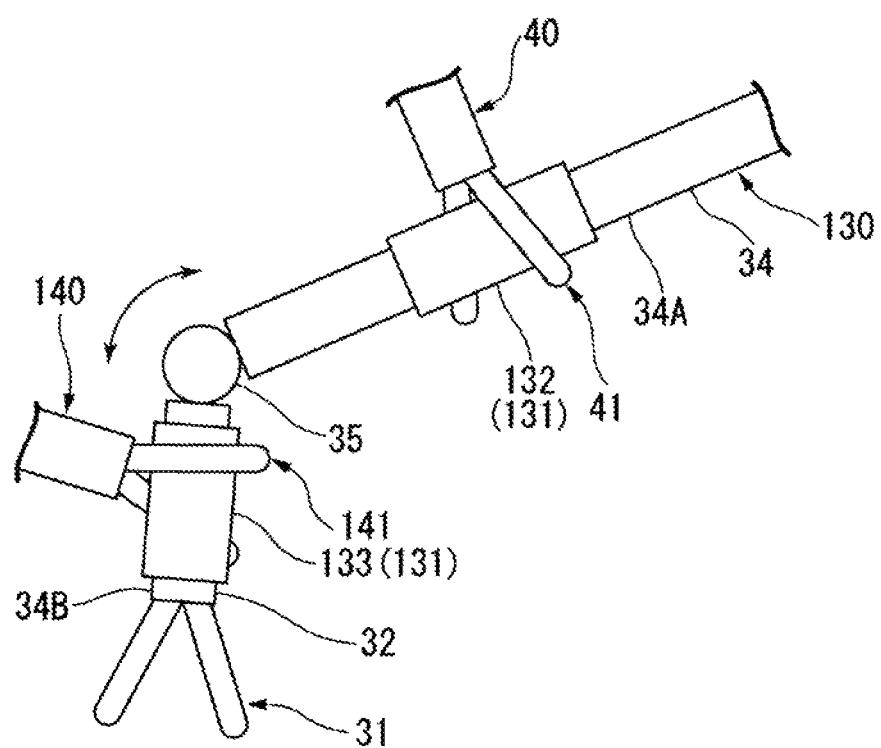
FIG. 14 is a view depicting on an enlarged scale a distal end side of a first medical instrument in the medical system according to the sixth embodiment.

With reference to FIGS. 13 and 14, a description will next be made about a sixth embodiment of the present disclosure.

FIG. 13 is a functional block diagram of a medical system 8 according to the sixth embodiment. FIG. 14 is a view depicting on an enlarged scale a distal end side of a first medical instrument 130 in the medical system 8.

As depicted in FIG. 13, the medical system 8 is different from the medical system 2 according to the second embodiment in that the first medical instrument 130 includes a contacted portion 131 in place of the contacted portion 61. It is to be noted that a detailed description is omitted herein about elements having similar configurations as in the medical system 2 according to the second embodiment.

The contacted portion 131 has a first contacted portion 132 and a second contacted portion 133. The first contacted portion 132 is disposed in the vicinity of the joint 35 on the proximal-side insertion portion 34A, in other words, at a position closer to the joint 35 than the proximal end portion 33 on the proximal-side insertion portion 34A and on an outer circumferential wall of the proximal-side insertion portion 34A. The second contacted portion 133 is disposed on an outer circumferential wall of the distal-side insertion portion 34B and between the joint 35 and the distal end portion 32.

The first contacted portion 132 and the second contacted portion 133 are configured substantially the same as the contacted portion 61 in the second embodiment. Therefore, the medical system 8 according to this embodiment is operated similar to the medical system 2 according to the second embodiment if only one of the first contacted portion 132 and the second contacted portion 133 is grasped by the second end effector 41 of the second medical instrument 40.

The contacted portion 131 is configured to enable control of the joint 35 only if the first contacted portion 132 and the second contacted portion 133 are grasped by the second end effector 41 of the second medical instrument 40 and a third end effector 141 of a third medical instrument 140 having substantially the same configuration as the second medical instrument 40, respectively. In other words, with both the first contacted portion 132 and the second contacted portion 133 being grasped, the bending angle of the distal-side insertion portion 34B can be adjusted relative to the proximal-side insertion portion 34A.

Described specifically, the control unit 20 performs the hereinbefore-described copying control on the joint 35 of the first medical instrument 130 if detection information, which indicates detection of a contact, have been received from both the first contacted portion 132 and the second contacted portion 133. As a consequence, the distal-side insertion portion 34B can be bent to a desired position relative to the proximal-side insertion portion 34A by operating the second end effector 41 and the third end effector 141 as needed.

Owing to the configuration described hereinbefore, an operator Op can control bending movement of the joint 35 of the first medical instrument 130 by the second medical instrument 40 and third medical instrument 140 inside the body.

In sum, one aspect of the disclosed technology is directed to a medical instrument holding device comprises a holding portion configured to hold a first medical instrument having a first insertion portion to be inserted into an abdominal cavity of a patient. An arm is connected to the holding portion and including at least one joint. A base is connected to a proximal end side of the arm. A first sensor is configured to detect an external force caused by a second insertion portion of a second medical instrument in the abdominal cavity. A controller is configured to generate a first control signal for actuating the arm based on the external force detected by the first sensor.

The first insertion portion comprises a second sensor configured to detect contact of the second insertion portion to the first insertion portion. The controller is configured to receive a signal from the second sensor. The signal is indicating the detection of contact of the second insertion portion to the first insertion portion, acquires the external force detected by the first sensor and generates the first control signal to actuate the arm based on the acquired external force. The controller is configured to generate a second control signal to maintain the arm at the same position if the signal from the second sensor is no longer received while actuating the arm by the generated first control signal. The controller is configured to generate the first control signal based on the external force detected by the first sensor so that the first insertion portion inserted in the abdominal cavity through an abdominal wall has a pivot point at a crossing point between the first insertion portion and the abdominal wall. The controller is configured to generate the first control signal based on the external force detected by the first sensor so that the arm is actuated to cancel out the external force.

Another aspect of the disclosed technology is directed to a control method of a medical instrument holding device having a holding portion supporting a first medical instrument. The first medical instrument is inserted in an abdominal cavity of a patient. An arm is configured to enable a positional adjustment of the holding portion and comprises detecting an external force applied from a second medical instrument to the first medical instrument in the abdominal cavity, generating a first control signal to actuate the arm based on the detected external force, and actuating the arm based on the generated first control signal.

The control method of the medical instrument holding device further comprises generating a second control signal to maintain the arm at the same position if the external force is no longer detected while the arm is being actuated by the first control signal and actuating the arm based on the generated second control signal. The first control signal is generated based on the detected external force so that the first medical instrument inserted in the abdominal cavity through an abdominal wall has a pivot point at a crossing point between the first medical instrument and the abdominal wall. The first control signal is generated based on the detected external force so that the arm is actuated to cancel out the external force.

A further aspect of the disclosed technology is directed to a medical system comprises a first medical instrument and a second medical instrument configured to engage with the first medical instrument to perform an operation inside an abdominal cavity of a patient. The first medical instrument includes an elongated insertion portion having respective opposed distal and proximal end portions. The distal end portion is engaged with the second medical instrument and the proximal end portion is attached to a medical instrument holding device. The medical instrument holding device comprises respective base and holding portions being coupled to one another by respective at least one arm and at least one joint. The arm includes at least one first sensor configured to detect an external force caused by the second medical instrument during the operation inside an abdominal cavity of a patient. A control unit is configured to be in electrical communication with the at least one arm to generate a first control signal and to actuate the least one arm based on the external force detected by the first sensor. The respective at least one arm and the at least one joint is defined by a plurality of arms and a plurality of joints attached to one another, respectively.

INDUSTRIAL APPLICABILITY

According to the hereinbefore-described embodiments and modifications of the present disclosure, it is possible to provide a medical instrument holding device and a medical system, both of which allow an operator to easily move a medical instrument, which is held on an arm portion, to a desired position, an operating method of the medical instrument holding device, and an operating method of the medical system.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

The preferred embodiments and modifications have been described hereinbefore, but the present disclosure should not be limited to these embodiments and modifications. Addition, omission and substitution of one or more configurations and other changes are feasible within a scope not departing from the spirit of the present disclosure.

NUMERAL REFERENCE LIST 1, 2, 3, 4, 5, 6, 7, 8 Medical system
10, 70, 90, 100 Medical instrument holding device
11 Holding portion
12 Arm portion
13 Joints
15 Base portion
16 Force detecting portion
20 Control unit
30, 60, 80, 110, 120, 130 First medical instrument
31 First end effector
40 Second medical instrument
41 Second end effector
42 Operating portion
61, 62, 81, 121, 131 Contacted portion
63 Contact sensor (contact detecting portion)
101 Display unit
122 Operation instructing portion
F1, F2 External force

What is claimed is:

1. A medical instrument holding device comprising:
a holding portion configured to hold a first medical instrument having a first insertion portion to be inserted into an abdominal cavity of a patient;
an arm connected to the holding portion and including at least one joint;
a base connected to a proximal end side of the arm;
a first sensor configured to detect an external force caused by a second insertion portion of a second medical instrument in the abdominal cavity; and
a controller configured to generate a first control signal for actuating the arm based on the external force detected by the first sensor.

2. The medical instrument holding device of claim 1, wherein
the first insertion portion comprises a second sensor configured to detect contact of the second insertion portion to the first insertion portion, and
the controller is configured to:
receive a signal from the second sensor, the signal is indicating the detection of contact of the second insertion portion to the first insertion portion;
acquire the external force detected by the first sensor; and generate the first control signal to actuate the arm based on the acquired external force.

3. The medical instrument holding device of claim 2, wherein
the controller is configured to generate a second control signal to maintain the arm at the same position if the signal from the second sensor is no longer received while actuating the arm by the generated first control signal.

4. The medical instrument holding device of claim 1, wherein
the controller is configured to generate the first control signal based on the external force detected by the first sensor so that the first insertion portion inserted in the abdominal cavity through an abdominal wall has a pivot point at a crossing point between the first insertion portion and the abdominal wall.

5. The medical instrument holding device of claim 1, wherein
the controller is configured to generate the first control signal based on the external force detected by the first sensor so that the arm is actuated to cancel out the external force.

6. A control method of a medical instrument holding device having a holding portion supporting a first medical instrument, the first medical instrument being inserted in an abdominal cavity of a patient, and an arm configured to enable a positional adjustment of the holding portion, comprising:
detecting an external force applied from a second medical instrument to the first medical instrument in the abdominal cavity;
generating a first control signal to actuate the arm based on the detected external force; and
actuating the arm based on the generated first control signal.

7. The control method of the medical instrument holding device of claim 6, further comprising:
generating a second control signal to maintain the arm at the same position if the external force is no longer detected while the arm is being actuated by the first control signal; and
actuating the arm based on the generated second control signal.

8. The control method of the medical instrument holding device of claim 6, wherein
the first control signal is generated based on the detected external force so that the first medical instrument inserted in the abdominal cavity through an abdominal wall has a pivot point at a crossing point between the first medical instrument and the abdominal wall.

9. The control method of the medical instrument holding device of claim 6, wherein
the first control signal is generated based on the detected external force so that the arm is actuated to cancel out the external force.

10. A medical method comprising:
inserting a first medical instrument into an abdominal cavity of a patient;
holding the first medical instrument by a medical instrument holding device;
inserting a second medical instrument into the abdominal cavity along a path different from the first medical instrument;
operating the second medical instrument so that the second medical instrument comes into contact with the first medical instrument in the abdominal cavity;
applying an external force from the second medical instrument to the first medical instrument, the first medical instrument being in contact with the second medical instrument, in the abdominal cavity;
detecting the external force by the medical instrument holding device;
operating the first medical instrument based on the external force detected by the medical instrument holding device so that the first medical instrument moves to a desired position;
eliminating the contact of the second medical instrument to the first medical instrument; and
operating the medical instrument holding device so that the first medical instrument remains at the desired position.

11. A medical system comprising:
a first medical instrument; and
a second medical instrument configured to engage with the first medical instrument to perform an operation inside an abdominal cavity of a patient wherein
the first medical instrument includes an elongated insertion portion having respective opposed distal and proximal end portions wherein the distal end portion being engaged with the second medical instrument and the proximal end portion being attached to a medical instrument holding device,
the medical instrument holding device comprises respective base and holding portions being coupled to one another by respective at least one arm and at least one joint,
the arm includes at least one first sensor configured to detect an external force caused by the second medical instrument during the operation inside an abdominal cavity of a patient, and
a control unit configured to be in electrical communication with the at least one arm to generate a first control signal and to actuate the least one arm based on the external force detected by the first sensor.

12. The medical system of claim 11, wherein the respective at least one arm and the at least one joint is defined by a plurality of arms and a plurality of joints attached to one another, respectively.

* * * * *